(12) United States Patent
Eichmann et al.

(10) Patent No.: US 11,268,919 B2
(45) Date of Patent: *Mar. 8, 2022

(54) THERMAL ANALYSIS FOR SOURCE ROCKS

(71) Applicant: Saudi Arabian Oil Company, Dhahran (SA)

(72) Inventors: Shannon L. Eichmann, Katy, TX (US); Katherine Leigh Hull, Houston, TX (US); Younane N. Abousleiman, Norman, OK (US); David Jacobi, Spring, TX (US)

(73) Assignee: Saudi Arabian Oil Company, Dhahran (SA)

( * ) Notice: Subject to any disclaimer, the term of this patent is extended or adjusted under 35 U.S.C. 154(b) by 363 days.

This patent is subject to a terminal disclaimer.

(21) Appl. No.: 16/569,474

(22) Filed: Sep. 12, 2019

(65) Prior Publication Data

US 2021/0080414 A1    Mar. 18, 2021

(51) Int. Cl.
  *G01N 25/18*  (2006.01)
  *G01K 13/00*  (2021.01)
  *G01K 15/00*  (2006.01)
  *G01J 5/00*  (2006.01)
  *G01Q 60/24*  (2010.01)

(52) U.S. Cl.
  CPC .......... *G01N 25/18* (2013.01); *G01Q 60/24* (2013.01)

(58) Field of Classification Search
  USPC ............................. 374/44, 141, 1, 121, 136
  See application file for complete search history.

(56) References Cited

U.S. PATENT DOCUMENTS

| | | |
|---|---|---|
| 5,441,343 A | 8/1995 | Pylkki et al. |
| 6,095,679 A | 8/2000 | Hammiche et al. |
| 6,491,425 B1 | 12/2002 | Hammiche et al. |
| 7,086,484 B2 | 8/2006 | Smith |
| 8,177,422 B2 | 5/2012 | Kjoller et al. |
| 9,128,210 B2 | 9/2015 | Pomerantz |
| 9,696,270 B1 | 7/2017 | Roy et al. |
| 2012/0026037 A1 | 2/2012 | Thomson et al. |
| 2014/0048694 A1 | 2/2014 | Pomerantz |
| 2017/0336528 A1 | 11/2017 | Badri et al. |
| 2021/0080413 A1 | 3/2021 | Eichmann et al. |

FOREIGN PATENT DOCUMENTS

| | | | |
|---|---|---|---|
| CN | 87213495 U | * | 6/1988 |
| CN | 106525898 A | * | 3/2017 |
| KR | 101384986 B1 | * | 4/2014 |

(Continued)

OTHER PUBLICATIONS

Asylum Research MFP-3D (Year: NA).*

(Continued)

*Primary Examiner* — Mirellys Jagan
(74) *Attorney, Agent, or Firm* — Fish & Richardson P.C.

(57) ABSTRACT

A system and method for evaluating a geological formation including subjecting a source-rock sample from the geological formation to atomic force microscopy (AFM) to determine a thermal property or material property of the source-rock sample. The properties determined may include thermal conductivity or material transition temperature.

35 Claims, 10 Drawing Sheets

(56) References Cited

FOREIGN PATENT DOCUMENTS

WO     WO 2010019256     2/2010

OTHER PUBLICATIONS

PCT International Search Report and Written Opinion in International Appln. No. PCT/US2020/05343, dated Feb. 5, 2021, 14 pages.

PCT International Search Report and Written Opinion in International Appln. No. PCT/US2020/050337, dated Feb. 4, 2021, 13 pages.

Biot et al., "Temperature analysis in hydraulic fracturing," Journal of Petroleum Technology, vol. 39, No. 11, Nov. 1987, 9 pages.

Cahill et al., "Nanoscale Thermal Transport II," Applied Physics Reviews 1.1, 2014, 46 pages.

Cahill et al., "Nanoscale thermal transport," Journal of applied physics vol. 93, No. 2, Jan. 2003, 28 pages.

Esfahani et al., "Quantitative nanoscale mapping of three-phase thermal conductivities in filled skutterudites via scanning thermal microscopy," Nature Science Review, vol. 5, Issue 1, Feb. 2017, 31 pages.

Klapetek, "Chapter 11: Thermal Measurements," Quantitative Data Processing in Scanning Probe Microscopy: SPE Applications for Nanometrology, 2018, 26 pages.

Pollock and Hammiche, "Micro-thermal analysis: techniques and applications," Journal of Physics D: Applied Physics, vol. 34.9, 2001, 31 pages.

Tabatabaei et al., "Well performance diagnosis with temperature profile measurements," in SPE Annual Technical Conference and Exhibition, Society of Petroleum Engineers, Oct. 30-Nov. 2, 2011, published Jan. 2011, 16 pages.

Yang et al., "Nanoscale geochemical and geomechanical characterization of organic matter in shale," Nature Communications, vol. 8, 2179, Dec. 19, 2017, 9 pages.

\* cited by examiner

FIG. 5

| Shale | Quartz | Albite | K-Feldspar | Mica-Ill-Smec | Chlorite | Kaolinite | Calcite | Dolomite | Siderite | Pyrite | Marcasite | Anatase | Apatite | Halite | Anhydrite | Gypsum |
|---|---|---|---|---|---|---|---|---|---|---|---|---|---|---|---|---|
| 1 | 11 | 2 | 3 | 61 | 9 | 7 | 1 | 0 | 1 | 5 | 0.4 | 0.6 | 0.0 | 0.0 | 0.0 | 0.3 |
| 2 | 10 | 5 | 4 | 47 | 5 | 10 | 0 | 2 | 1 | 14 | 3.5 | 0.2 | 0.1 | 0.3 | 0.5 | 0.0 |
| 3 | 24 | 7 | 14 | 37 | 4 | 5 | 1 | 0 | 0 | 6 | 1.3 | 0.8 | 0.0 | 0.3 | 0.3 | 0.0 |

THERMAL ANALYSIS FOR SOURCE ROCKS

TECHNICAL FIELD

This disclosure relates to analysis of a geological formation having organic sources of hydrocarbons.

BACKGROUND

Unconventional source rocks may be organic-rich sedimentary deposits, such as shales and mud rocks. The organic components of the source shale may consist of the hydrocarbon-source material kerogen and its produced components bitumen and pyrobitumen. The mechanical, physical, and chemical properties of composites of the organic components and inorganic components (for example, silicates, clays, carbonates, and pyrite) forming the source rock fabric may affect predictive reservoir modeling, wellbore drilling, and economical oil and gas production.

SUMMARY

An aspect relates to a method of evaluating a geological formation. The method includes preparing a source-rock sample from the geological formation and acquiring a topography map of a region of the source-rock sample at a resolution less than 1 micrometer ($\mu m$). The method includes selecting measurement areas of the region based on the topography map and determining, via atomic force microscopy (AFM), thermal conductivity of the source-rock sample at the measurement areas at a scale less than 1 millimeter.

Another aspect relates to a method of evaluating a geological formation. The method includes mounting a source-rock sample from the geological formation to a sample holder of an AFM instrument. The method includes identifying a region of interest of the source-rock sample via a reflected-light optical image of the source-rock sample. Alternatively, the region may be identified by imaging and spectroscopy data types other than a reflected-light optical image, such as scanning electron microscopy (SEM), energy dispersive spectroscopy (EDS), fluorescence, AFM-infrared red (IR), and Fourier-transform infrared spectroscopy (FTIR). The method includes determining thermal conductivity of the region via the AFM instrument in scanning thermal microscopy (SThM) mode. The AFM instrument employs a cantilever having a cantilever tip.

The details of one or more implementations are set forth in the accompanying drawings and the description to be presented. Other features and advantages will be apparent from the description and drawings.

BRIEF DESCRIPTION OF DRAWINGS

FIG. 5 is a table giving mineralogy for source-rock (shale) samples in the Examples.

DETAILED DESCRIPTION

Figure 1:
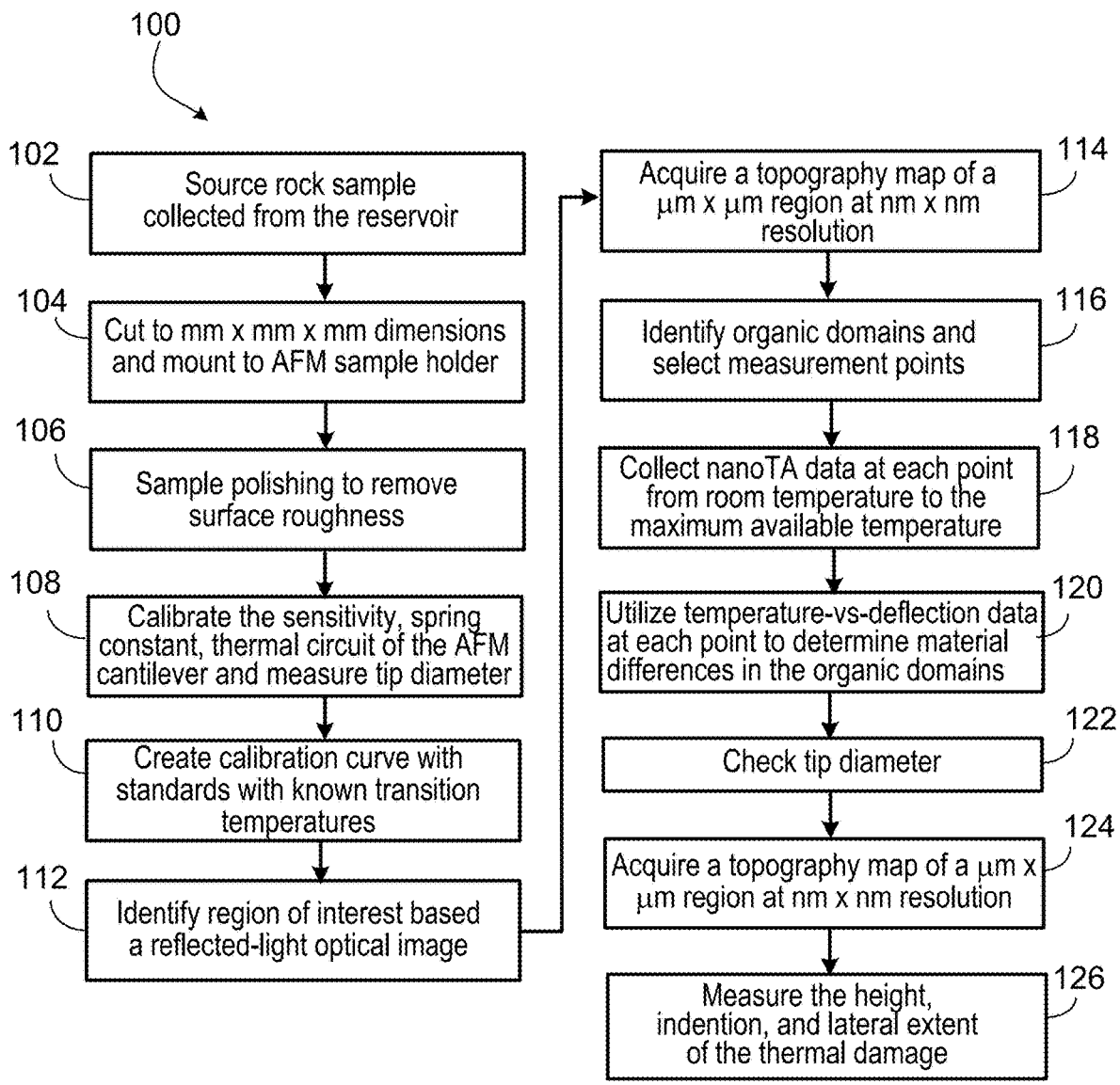
FIG. 1 is a block flow diagram of a method of nanothermal analysis of source rocks.

Some embodiments of the present disclosure relate to thermal analysis of porous composites, such as source rock shale having organic and inorganic structures with hydrocarbons. Aspects may include thermal analysis of rock or shale and organic components in composite structures from a geological formation (for example, shale formation) in which the organic components may be organic source material for hydrocarbons. Thermal properties of the conglomerate shale material, the segregated granular rock, and the organic domains may be considered. The thermal properties evaluated may include thermal conductivity and material transition temperature. The resolution of the thermal analysis may be at microscale or nanoscale via atomic force microscopy (AFM). Thermal modules associated with the AFM instrument or microscope may facilitate determination of thermal parameters (for example, thermal conductivity and transition temperature) to capture the thermal properties of individual features. The properties and the effects of individual components may be isolated and upscaled to an understanding of the macroscale behavior.

Aspects of the disclosure are directed to nanoscale and microscale measurements of the thermal properties (for example, thermal conductivity or material transition temperature) of rock formations (for example, shale or source rock) at the scale of the micro-heterogeneity and nano-heterogeneity of the composite rock components. The rock formation can include inorganic materials in the form of minerals and clays and organic materials in the form of kerogen, bitumen, and pyrobitumen. The nanoscale measurements can be by atomic force microscopy (AFM) for capturing thermal conductivities of source-rock samples at microscale or nanoscale resolution. The AFM instrument modes include at least nanothermal analysis (nanoTA) and scanning thermal microscopy (SThM). Nanoscale and microscale measurements of a thermal property can provide for a correlation between lithology, organic matter type and maturity, and the thermal property. The measurements may additionally account for the effects of structural anisotropy at the length scale of the rock fabric individual components. The collected data and associated analysis may be used as inputs to supplement basin modeling and well-production performance analysis. The well-production analysis may include improving or optimizing hydraulic fracturing operations.

The thermal conductivity of geological rock formations of a hydrocarbon reservoir may be utilized as a parameter for enhancing reservoir modeling reservoir and dating various basin properties. The thermal conductivity of rock formations may be utilized to predict or diagnose well production performance. The temperature profile of a well is a component of production logs and continues to be a routine measurement during production logging. Translation of the temperature profile into interpretations of the subterranean state may benefit from thermal conductivity information about the formation. Typically, the thermal conductivity (k) is taken as an average value and is assumed based on the lithology. This assumption, however, does not take into account the variations in the lithology versus depth which can affect the thermal conductivity. The ability to directly measure the thermal conductivity of each rock component at the scale of the heterogeneity has generally not been possible with conventional measurement of thermal conductivity.

A nanoscale measurement of thermal conductivity of samples of the rock formation can provide a correlation between lithology, organic matter type and maturity, and thermal conductivity. The correlation can be utilized in algorithms where thermal conductivity is not constant but a function of the other parameters. Direct nanoscale measurements of the thermal conductivity may additionally account for the effects of anisotropy at the length scale of the rock-fabric heterogeneity.

Aspects of the present disclosure provide nanoscale and microscale measurement via AFM to capture high-resolution (for example, nanoscale-resolution) measurement of thermal conductivities of source rocks (the source rock formation of the reservoir). Two applications for the information captured in this manner include: (1) basin modeling and (2) well production performance analysis.

Basin modeling may be employed to explain the amount and timing of hydrocarbons produced from a source (reservoir) and determine the migration pathway. A component of basin modeling is to evaluate the thermal history of the basin and thus explain the amount and types of hydrocarbons produced. The thermal history evaluation may be based on heat flow (Q) where the thermal conductivity in the i and j directions, $k_{ij}$, is a constant multiplier of the temperature gradient (dT) by depth (z) as shown in the following equation [1]:

$$Q = -k_{ij} \frac{dT}{dz} \quad [1]$$

The microscale or nanoscale resolution of thermal conductivity data from AFM may provide improved resolution of the components and their individual contribution to the overall heat flow in a basin model. The thermal conductivity at this resolution can provide insight into porosity development in kerogen.

In the second application (analysis of well production performance) related to the production performance of oil and gas wells, well conditions can be diagnosed with temperature logs and formation parameter values (including thermal conductivity). The diagnosis of the well conditions can include: (a) locating gas or water entries into production wells; (b) locating lost circulation zones; (c) detecting channels behind casing in the wellbore; and (d) analyzing stimulation treatments (for example, acidizing or fracturing) in terms of fluid placement.

AFM is a nanoscale characterization technique in which the deflection of a cantilever is employed to measure tip-surface interactions. As the tip of the cantilever interacts with the surface of a material (sample), two curves of force-versus-distance are generated. The two curves can be utilized to interpret material properties, such as mechanical moduli, surface topography, and adhesion. The traditional AFM probe is a cantilever of measurable spring constant with a pointed tip (AFM tip) having a radius in the range of 5 nanometers (nm) to 100 nm. The terms "AFM tip" or "tip" refer to a tip portion of the cantilever of an AFM instrument or device. In contact mode, the tip moves along the surface and the deflection of the cantilever is measured to produce a topography map at Angstrom resolution in height and on the nanometer (nm) scale laterally. Other AFM modes include tapping, force volume, and intermittent contact.

Embodiments of the present techniques are related to AFM determining or measuring of thermal properties (at nanoscale) of source rocks including their organic matter. The thermal properties determined or measured include material transition temperature and thermal conductivity. This technique may gather nanoscale and microscale resolution information for modeling and for a framework to recognize the nanocomposite nature of these materials. This recognition may impact understanding of hydrocarbon generation, micro-migration, macro-migration, reservoir storativity, reservoir production, and micro-porosity (and nano-porosity) development in the organic matter. In addition, models capturing temperature changes of the formation or fluids upon injection into the formation may utilize the nanoscale thermal-conductivity measurements to predict success of well and formation treatments.

When thermal properties are determined or measured by AFM, a cantilever modified to have a heating element, such as a metal film or resistive heater (for example, printed metal circuit), is employed in place of the standard cantilever. A voltage can be applied across the metal film that creates the heating circuit to control the temperature of the AFM cantilever tip (tip portion) at the end of the cantilever. In implementations, a change in voltage difference due to changes in the circuit resistance during the AFM tip interaction with the sample may be correlated with sample thermal properties.

The "heating element" on the AFM cantilever may be a resistive heater, such as a printed metal circuit or metal coating. The metal coating may be a metal coated as a metal resistor on the cantilever tip portion. In operation, the voltage difference (for example, delta voltage or ΔV as input voltage minus output voltage) across the heating element may be measured to monitor heat transfer to and from the tip. Heat transfer between the tip and the environment or between the tip and a mounted sample may change the voltage difference across the heating element.

In certain implementations, a voltage may be applied to the heating element to set the tip to a set-point temperature and maintain the tip at the set-point temperature. A first voltage difference across the heating element can be measured with the tip not interacting with the sample (for example, at least 5 mm distant from the sample). A second voltage difference across the heating element can be measured with the tip interacting with the sample and transferring heat to the sample. The change in voltage difference from the first voltage difference to the second voltage difference can be correlated with thermal properties (for example, thermal conductivity) of the sample. In an implementation with the tip, for example, at room temperature and the tip then receiving heat from a heated mounted source-rock sample, the resulting change in voltage difference across the heating element can be measured and correlated with thermal properties of the sample.

A calibration curve(s) may be employed to correlate a measured change in voltage difference across the heating element with a value of a thermal property of the sample. Calibration curves may be generated, for example, by measuring the change in voltage difference for samples of standards or materials having known thermal properties.

To determine or measure the nanoscale thermal properties of source rocks and organic matter, certain embodiments employ at least two modes of operation: (1) nanothermal analysis (nanoTA) and (2) scanning thermal microscopy (SThM). In nanothermal analysis, the aforementioned heating element may be employed to ramp the cantilever tip temperature.

In nanoTA as a mode of operation, the AFM tip is placed in contact with the sample. The tip temperature is ramped (an increasing ramp) and the deflection of the cantilever is recorded at preselected positions on the sample. The preselected positions may be specified by the user. The cantilever movement versus temperature is utilized to measure the transition temperatures of the material position-by-position or point-by-point (or area-by-area). In nanoTA, a point may be selected but because the AFM tip has a radius and shape, the AFM tip contacts an area at that point. Thus, selection of a measurement point may be selection of a measurement area. While the AFM tip may have an end surface, the AFM tip is a tip portion of the AFM device cantilever and has a radius or width in the range of 5 nm to 100 nm.

Traditionally, material transition temperatures are utilized to understand the glass transition temperature (Tg) and melting point (Tm) of polymeric materials where these parameters are measured from a deflection-versus-tip temperature curve at selected locations. Initially, the nanoTA probe (cantilever) may be used to generate an AFM image that allows the user to identify points (positions or areas) for local thermal property information. After the point of interest is selected, the probe is moved to the fixed point on the sample surface. The temperature of the tip may then be ramped linearly with time while the degree of bending (deflection, movement) is monitored. At the phase transition, the sample material beneath the tip softens and the probe penetrates into the sample. This process provides the nanoscale equivalent of a bulk thermo-mechanical analysis that measures the phase transition temperatures of the sample (such as Tg or Tm).

Employing nanoTA for source-rock samples provides an opportunity to explore properties of the organic components (for example, kerogen, bitumen, and pyrobitumen) and inorganic components (for example, silicates and clays) in the natural intertwined structure of the organic and inorganic components. Such is generally not possible with typical thermal analysis techniques that require bulk shale samples, separate clay minerals, or isolated kerogen powder where bitumen has already been extracted. The cantilever deflection versus temperature can be used to understand the transition temperatures and the thermal strains of the organic matter within domains having organic and inorganic components. This may also facilitate distinguishing components of the organic matter (for example, bitumen, kerogen, and pyrobitumen) at the submicron scale.

Distinguishing kerogen, bitumen, and pyrobitumen has implications for unconventional source-rock stimulation treatments. Recently-developed kerogen control fluids for breaking down elastomeric ductile organic matter during the hydraulic fracturing treatment may be selective for kerogen. Distinguishing organic matter types within intact source-rock samples in the laboratory may facilitate predicting the success of well and formation treatments in field applications.

In addition, the change in the transition temperatures and shape (behavior) of the measured cantilever deflection-versus-temperature curves can provide information about sample maturity and how the properties (for example, porosity, viscosity, ductility, and crosslink density) of the kerogen change as the source-rock samples mature. This may be of particular importance to understanding hydrocarbon storage, expulsion, and micro-migration and macro-migration within the basin with changes in pressure, temperature, and stress geologic evolution. In addition to the typical use of the deflection-versus-temperature data, the topography of the sample after the temperature ramp (particularly the topography of the spot where nanoTA was performed) may be utilized to provide further information about the local heat transfer in the organic domains and the surrounding minerals. For instance, the lateral extent of permanent deformation, the height change beyond the central tip location, and the depth of the indention at the tip position may be linked to the thermal deformation (strain) and maturation properties of the organic matter.

In SThM as a mode of operation, the AFM tip is rastered along the sample surface while the AFM control loop for heating the tip measures the difference between the input voltage and the output voltage (for example, across the metal resistor coated on the AFM device cantilever). The voltage difference may be measured across a heating element (for example, metal resistor or printed metal circuit) on the tip portion of the AFM cantilever. When the tip is away from the sample, the voltage difference is related to heat loss due to ambient conditions. When the tip comes in contact with the sample, heat may flow from the tip to the sample and the voltage difference is monitored. The more thermally conductive the area, the greater the voltage difference (more negative) and the image pixel is dark. By contrast, when an area is less thermally conductive, the voltage difference is smaller (less negative) and the image pixel is bright.

For three dimensional (3D) composite materials with nanoscale chemical heterogeneities, the bulk thermal conductivity is related to the thermal conductivity of the individual components that make up the material and how those materials are distributed within the composite. Source rock is a mix of organic and inorganic materials that varies texturally, mechanically, and chemically at the nanoscale and microscale. The composite can be described as a natural 3D composite material. The AFM may determine or measure the thermal conductivity of source rocks at length scales of nanometer (nanoscale), micrometer (microscale), and millimeter scale. At each of these length scales, the thermal conductivity of minerals and organics of the source-rock matrix can be interrogated with respect to lithology, mineralogy, and thermal maturity. In addition to measuring the thermal conductivity of the individual components, AFM can be employed to understand the thermal conductivity differences due to component shape, orientation, bedding (stacking), and average values of upscaled properties. This may differ from measurements made on bulk (macro) samples at less resolution.

A factor that affects thermal conductivity is the size of the domains in the composite material which can vary in source rocks. Scattering at material interfaces reduces thermal conductivity but interrogating these effects conventionally at the nanoscale can be problematic. Conversely, utilizing AFM to link the thermal conductivity of a source rock to the grain or domain size (rock texture) provides for thermal-conductivity estimates for models and upscaling. The AFM determination or measurement of thermal conductivity can be performed at the multiple scales including nanoscale, microscale, and millimeter scale. These data may provide a framework of the thermal-conductivity parameters utilized in basin models. Rather than assign thermal conductivity based on lithology alone, the effects of mineralogy and thermal maturity can be taken into account.

The thermal conductivities when upscaled can additionally be utilized to understand the rate of change of the fracturing fluid or the source-rock formation during hydraulic fracturing treatment. This may be beneficial for reactive hydraulic fracturing fluids (for example, kerogen control fluid) where the activation temperature of the reaction should be reached in order for kerogen to begin to degrade upon contact with the fluid. The greater the thermal conductivity of the formation (particularly the organic domains), the more quickly the fluid and the kerogen reach the activation temperature (and the kerogen begins to degrade). This knowledge of the temperature profile at the microscale and nanoscale of the interfaces between the formation and fluid may facilitate understanding of how the kerogen properties can be altered within the same time scale as a given stage in a hydraulic fracturing treatment.

In SThM, the topography may be utilized to identify domains, pores, surface contamination, or surface structures that may affect the voltage difference across the heating element (metal film or printed circuit) on the AFM tip. An estimate of porosity of the organic domains in intact rock may be determined via SThM measurements. The combination of SThM with topography maps can be utilized to estimate pore sizes and shapes. The estimated pore sizes and shapes can be correlated to the effect of porosity increase and decrease on the thermal properties of the rock. Kerogen porosity is typically estimated from imaging techniques or by gas sorption techniques. For source rocks, pores are complex with varying size, shape, and orientation that develop because of hydrocarbon generation and in providing the initial hydrocarbon migration pathway.

Differences in thermal conductivity can be related to the scattering of phonons. Therefore, SThM may provide for measuring or determining porosity in the organic domains of kerogen at greater resolution than provided by other techniques. The ability to identify and characterize these nanopores gives not only understanding of hydrocarbon generation and storage, but also the potential for liquid or gas (for example, carbon dioxide or $CO_2$) uptake during stimulation treatments. In addition, the evolution of thermal conductivity versus maturation can be evaluated by artificially maturing a sample while tracking differences in thermal conductivity and porosity variations. This may provide insight into pore development and pore characteristics (pore shape and size) at the nanometer scale as well as at the length-scale of the whole organic domain of the sample. The thermal conductivity of kerogen pores that are both evacuated and fluid-saturated can also be measured and analyzed.

Graphene is commonly used as a filler material to produce thermally conductive polymeric composites where the amount of graphene dispersed in an insulating polymer matrix provides increased thermal conductivity. The thermal conductivity of the organic domains as determined or measured by SThM may also provide a relative comparison of thermal maturity between samples. As kerogen matures, aliphatic domains (having less thermal conductivity than other domains) become increasingly more aromatic and thus more graphitic. In present embodiments, the thermal conductivity of organic domains in a series of samples with unknown thermal maturity can be compared to give the relative difference in thermal conductivity. This relative difference can then be utilized to identify more mature from less mature samples as well as provide information about the local distribution of the graphitic versus aliphatic components.

Present embodiments provide techniques to employ AFM to determine or measure the thermal conductivity of source rocks at the length scale of the individual rock components. The techniques may also determine or measure the anisotropy of the thermal conductivity of the components of source rocks at the micrometer and nanometer scales. Also included is determining or measuring thermal expansion (alteration) of the organic components properties at the submicron scale. These thermal expansion data may be linked to the thermal maturity and, in some cases, the crosslink density of the kerogen. Such may be relevant for gas and oil storage, expulsion, and migration.

In the nanoTA mode of operation, topography and mechanical properties scans of a source-rock sample are collected to identify regions of interest (organic domains) for measuring glass transition and melting points. Once an organic domain is recognized, individual measurement points are identified by the user for thermal analysis. Next, at each point, the AFM tip is placed on the surface and the temperature at the tip ramps from an initial set-point temperature (for example, room temperature) to a predetermined maximum temperature (for example, up to 500° C.) while the deflection of the cantilever is recorded. After data is collected during the heat ramps at each position, final topography and mechanical properties scans may be taken. Phase transitions of the organic domains may be identified based the deflection-versus-temperature curve. In addition, the technique may interrogate the after-image of the domain for the lateral effects of the local heating as demonstrated by the size and shape of the local area. Both the transition temperatures and the extent of the thermal expansion (damage) may then be correlated to the thermal maturity and the crosslink density of the organic domains. An exemplary general procedure for data collection and analysis by applying nanoTA mode on source rocks is provided in FIG. 1.

Thermal conductivity may be what affects the measured voltage change across the tip resistor (for example, printed metal circuit) in the AFM instrument in the SThM mode. Variations in that voltage difference may map on a single sample and may be related to differences in the thermal conductivity of different components. The measuring of thermal conductivity may be labeled as an indirectly measuring the thermal conductivity or as determining the thermal conductivity. A calibration curve may be employed to convert the measured voltage change to thermal conductivity.

In implementations of AFM SThM and AFM nanoTA, a voltage may be applied across a metal printed circuit on the cantilever to heat the tip portion at the end of the cantilever. The applied voltage may be utilized to set, maintain, regulate, or ramp the temperature at the end of the tip. A trace voltage may be applied when (as in cases of SThM) the desired tip temperature is at or near room temperature.

In some cases with the tip is at temperature equilibrium, the voltage difference ($\Delta V$) may be zeroed (for example, the actual non-zero $\Delta V$ assigned a zero value). The step to zero the system is most commonly done when the tip is far (for example, at least one millimeter) from the surface to correct for the ambient thermal losses.

In some implementations of SThM, a voltage may be applied across the metal printed circuit to maintain the tip at a constant set-point temperature. Prior to interaction of the tip with the mounted sample, the voltage difference across the metal printed circuit to maintain the tip at set-point temperature may be measured. Then, when the tip interacts with the sample and with heat transfer between the tip and sample, the voltage difference across the metal printed circuit to maintain the tip at set-point temperature will change because of the heat transfer. The voltage difference may be affected with heat transfer from the tip to the sample or from the sample to the tip.

In SThM, when the tip is in contact with a source-rock sample mounted in the AFM device, the voltage difference may change. The change may be due, for example, to heat leaving the tip (heat transfer from the tip to the sample) and the associated change in the resistance across the printed circuit to maintain the tip temperature at set point. The measured voltage difference may be converted to a value for thermal conductivity of the source-rock sample based on the aforementioned calibration curve. The conversion of the measured voltage difference to a value for thermal conductivity may be performed manually by a user. The conversion may be automated by a computing system associated with or coupled to the AFM device or automated by the AFM device. The computing system or the AFM device may store the calibration curve (or associated calibration equations).

In nanoTA mode, the cantilever deflection may be measured and related to material properties, such as thermal expansion, transition temperature, and crosslink density. These material properties can be linked to organic material type and maturity. Thermal expansion may be the tendency of matter to change its shape, area, and volume in response to a change in temperature.

FIG. 1 is a method 100 of nanothermal analysis of source rocks. The method 100 includes data collection and analysis employing an AFM instrument in nanoTA mode on source rocks. For nanoTA, the AFM instrument (system) includes a temperature controller such as a thermal applications controller (TAC). The temperature controller and a heating element (for example, a printed metal circuit on a probe tip) may heat and control the temperature of the AFM instrument probe (cantilever) tip. In nanoTA, heat is transferred from the probe tip to the mounted source-rock sample.

The method 100 can repeat the depicted actions (block 102 to block 126) for several samples of source rock to correlate differences in thermal maturity, organic matter type, and crosslink density. The method 100 is a nanothermal analysis (nanoTA) procedure for source rocks of a geological formation such a shale formation.

At block 102, the method includes collecting a sample of source rock from the reservoir. The reservoir is the geological formation. The reservoir source rock can be an unconventional source-rock formation with organic matter including kerogen, bitumen, and pyrobitumen.

At block 104, the method includes preparing the source-rock sample for analyses. For instance, the source-rock sample may be cut to millimeter (mm) dimensions and then mounted to an AFM sample holder. In certain implementations, the source-rock sample is cut to generally a cuboid shape (for example, FIG. 4) and with length, width, and height each a few millimeters or centimeters (cm). The length and width can each be, for example in the range of 1 mm to 80 mm, 3 mm to 60 mm, or 5 mm to 40 mm. The height can be, for example, in the range of 0.5 mm to 20 mm, 1 mm to 15 mm, or 1 mm to 10 mm. Instead of cuboid, the sample may be prepared generally cylindrical having a diameter and thickness (height) each a few millimeters (for example, less than 50 mm). The sample may also be prepared as an irregular shape but with a surface available for analysis.

At block 106, the mounted cut sample is further prepared by polishing to remove surface roughness. For instance, a surface (for example, top surface) of the mounted cut sample may be polished to reduce the surface roughness to nanometers or micrometers. In implementations, the specified surface roughness for the polished surface is less than 15 µm, or in the ranges of 0.5 nm to 15 µm, 1 nm to 13 µm, or 1.5 nm to 10 µm. In certain embodiments, the sample surface may be polished mechanically and then finely polished via ion milling such as with an argon ion mill. Imaging and the AFM nanoTA mode may be performed on the polished surface.

At block 108, the method includes calibrating the AFM instrument. In particular, the method may include calibrating the sensitivity, spring constant, and thermal circuit of the AFM cantilever. Also, the diameter of the cantilever tip may be measured. The tip diameter may be measured because the tip diameter may partially control the contact area on the sample during analysis of the sample. The contact area may also be partially controlled by the sample surface. Over time in utilization of the AFM instrument, the cantilever tip may wear, which changes the contact area. Tracking the tip diameter can account for data effects caused by the changing contact. Tracking tip diameter may be typical for quantitative AFM measurements.

AFM gives nanoscale characterization by sensing deflection of the cantilever as affected by interactions of the tip with the sample surface. The AFM probe is the cantilever of measurable spring constant with the pointed tip having a radius, for example, in the range of 5 nanometers (nm) to 100 nm. The AFM cantilever may be, for example, a micro-machined silicon probe.

At block 110, the method includes generating a calibration curve with standards having known transition temperatures. The standards may be bulk materials of known thermal properties. Standards may be selected to generally represent the components in the source-rock samples. The standards may be prepared and mounted in the same or similar manner as the source-rock samples or can be fitted into a single respective holder as a mounted material. The generated calibration curve may be the measured AFM cantilever deflection or response versus the known transition temperature of interest or known crosslink density. The transition temperature may be the glass transition temperature ($T_g$) or melting point ($T_m$).

The generated calibration curve(s) may be employed in the AFM analysis of the source-rock samples. The response (cantilever deflection) of the AFM device to the organic domains in the source rock sample may be measured and the transition or alteration temperatures may be measured. By comparing this collected data of the actual source-rock sample to the calibration curve (the calibration set), polymeric or crosslinking states of the actual source-rock sample can be deduced or determined. The alteration temperature may be the temperature at the onset of damage (for example, burned or formation of ridges) on the sample.

At block 112, the method includes identifying a region of interest of the source-rock sample utilizing techniques, such as a reflected-light optical image, scanning electron microscopy (SEM), energy dispersive spectroscopy (EDS), fluorescence, AFM-infrared red (IR), or Fourier-transform infrared spectroscopy (FTIR). In one implementation, the region of interest is identified based on a reflected-light optical image.

The method includes determining a material property of organic domains of the region via the AFM instrument in nanothermal analysis (nanoTA) mode utilizing a reflected-light optical image or other techniques, such as SEM, EDS, AFM-IR, or FTIR. A microscope of the AFM instrument may capture the optical image. The region of interest may include organic compounds. The region of interest may include an intertwined structure of organic compounds and inorganic compounds. The evaluation of the optical image to identify a region of interest may consider shading in the reflected light images to select a region of interest having organic compounds. The organic domains may appear as a darker gray area that is amorphous. The gray color may vary depending on the samples, lighting, microscope, camera, and magnification but is generally distinguishable from other components. If desired to analyze organic domains, the subsequent selection of measurement areas within the region of interest may include selecting a measurement area having organic domains.

At block 114, the method includes acquiring a topography map of a micrometer (μm) region at nanometer resolution. The region may be the region of interest identified in block 112. The optical image may be used to identify the area to collect the topography map. The topography map may be, for example, of a region of 1 μm to 500 μm by 1 μm to 500 μm and at a resolution of 1 nm to 500 nm by 1 nm by 500 nm. The topographical map may be an image giving dimensions such as feature heights or elevations. The topographical image may have same resolution as the other AFM properties and in the same region as the AFM analysis. The topography map may be acquired via the AFM probe (cantilever). The topography map may be captured via contact, intermittent tapping, or tapping AFM modes where the AFM tip moves along or above the sample surface.

At block 116, the method includes identifying organic domains and selecting measurement points. The measurement points may be selected by a user. The organic domains identified and measurement points selected may be in the topographical map acquired in block 114 and in the region of interest of the sample as chosen in block 112.

At block 118, the method includes collecting nanoTA data at each selected measurement point over a temperature ramp, for example, from room temperature to the maximum available temperature. In implementations, the maximum available temperature may be 500° C. The maximum available temperature may be less than or more than 500° C. In nanoTA as an AFM mode of operation, the AFM tip is placed in contact with the sample surface and the tip temperature is ramped as the deflection of the cantilever is recorded at the preselected positions on the sample. The preselected positions include the measurement points selected by the user in block 116.

At block 120, the method includes utilizing temperature-vs-deflection data at each selected point to determine material differences in the organic domains. The temperature-vs-deflection data is nanoTA data collected in block 118. Employing nanoTA for source-rock samples provides an unconventional examination of properties of the organic components intertwined with inorganic components. The cantilever deflection versus temperature may be interpreted to distinguish components (for example, bitumen, kerogen, and pyrobitumen) of the organic matter at the submicron scale. The nanoTA data (block 118) and temperature-vs-deflection data (block 120) can be linked to the mineralogy and lithology as measured by other spectral techniques, such as energy dispersive spectroscopy (EDS) and scanning electron microscopy (SEM).

At block 122, the method includes checking the tip diameter. The diameter of the AFM cantilever tip may be measured to determine the change (if any) in tip diameter as compared to the value of tip diameter measured in block 108. The tip diameter may change because of damage to the tip or because of tip contamination that may affect tip sample contact.

At block 124, the method includes acquiring a topography map of a micrometer region at nanometer resolution. The acquisition of the topography map may be the same as the acquisition described at block 114. A reason to acquire this subsequent (second) topography map is to evaluate the impact of the thermal damage both laterally and vertically.

At block 126, the method includes measuring the height, indention, and lateral extent of the thermal damage. These measurements are made by using the topography map and image processing tools.

Lastly, the foregoing actions in block 102 through block 126 may be repeated for several samples of source rock to correlate changes in the extent of damage to differences in thermal maturity, organic matter type, and crosslink density.

In the SThM mode of operation, there are at least two methods (FIG. 2 and FIG. 3, respectively) to measure thermal conductivity. In the first method, heat transfer may occur from the AFM cantilever tip to the mounted sample. In the second method, the mounted sample is heated and heat transfer may occur from the mounted sample to the AFM cantilever tip. The variation between the two methods may be related to different aspects of the source rock.

The first method (FIG. 2) includes thermal conductivity measurements performed through the nanofabricated AFM tip. The tip may be held at a constant temperature while the sample is scanned. Additional scans can be performed at additional tip temperatures given by changing the applied voltage difference across the heating-element metal film or printed circuit on the cantilever tip portion.

In the first method, the AFM tip is rastered along the surface of the source-rock sample while a constant voltage is applied to the tip (for example, applied to the tip heating element). When the tip is away from the source rock, the voltage difference in the circuit to maintain the temperature set-point of the tip is related to heat loss due to ambient conditions. The voltage difference when away from the surface is commonly set to zero by adjusting the reference voltage prior to contact with this sample. This may be useful for quantitative analyses but can be optional. Assuming that the sample is cooler than the tip, the heat will flow from the tip to the sample. In this case, the resistance across the circuit printed on the cantilever changes and difference in the applied voltage (for example, to maintain the tip at a set point temperature) is measured. The more thermally conductive the nanoscale component (in the sample), the more heat flows from the tip. The voltage difference is proportionally large (more negative) and the pixel is dark. When a domain has low thermal conductivity, less heat flows from the tip and the difference is proportionally lower (less negative) and the area is bright.

In this first method, the thermal conductivity may be measured at each position (for example, on the order at tens of nanometers) in one orientation of the sample relative to the AFM tip. To study anisotropy, additional samples from the same source rock may be mounted in different orientations relative to the AFM tip and the thermal conductivity additionally measured at each position along the sample as the AFM tip is rastered along the sample surface. The actual temperature of the cantilever tip portion may be ramped to the set point temperature. The tip temperature may set to a specified temperature by setting the applied voltage or voltage difference across a heating element (for example, printed metal circuit) on the tip portion of the AFM cantilever. An implementation of this first method utilizing SThM for source-rock analysis is presented in FIG. 2.

Figure 2:
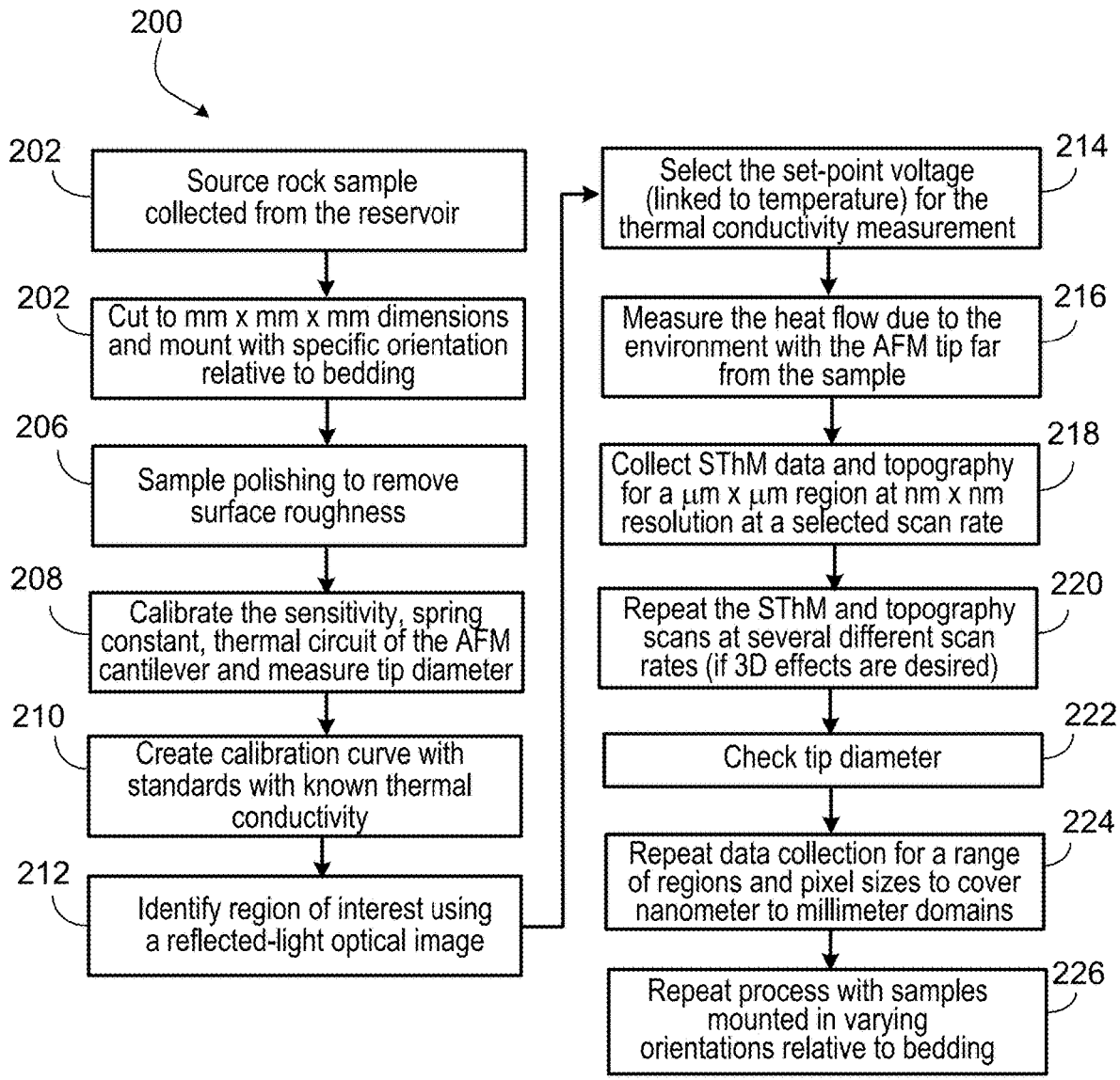
FIG. 2 is a block flow diagram of a method of scanning thermal microscopy of source rocks.

FIG. 2 is a method 200 of scanning thermal microscopy of source rocks. The method 200 includes the aforementioned first method utilizing SThM for source-rock analysis.

The method 200 is a scanning thermal microscopy procedure (first method) for source-rock analysis where the AFM tip.

The method determines thermal conductivity of minerals and organic domains found in the source rock. The method may link changes in the thermal conductivity to differences in the domain size, neighboring components, orientation, and thermal maturity.

At block 202, the method includes collecting a rock sample from the geological formation reservoir. The rock sample includes organic components and inorganic components.

At block 204, the method includes shaping (cutting) the source-rock sample to millimeter (mm) dimensions. The source-rock sample may be cut to generally a cuboid shape (for example, FIG. 4) with length, width, and height each a few millimeters or centimeters (cm). The length and width can each be, for example in the range of 1 mm to 80 mm, 3 mm to 60 mm, or 5 mm to 40 mm. The height can be, for example, in the range of 0.5 mm to 20 mm, 1 mm to 15 mm, or 1 mm to 10 mm. Instead of cuboid, the sample may be prepared generally cylindrical having a diameter and thickness each a few millimeters. The sample may also be prepared as an irregular shape but with a surface available for analysis.

The shaped sample may be mounted to an AFM sample holder. The sample may be mounted with a specific orientation relative to bedding in the sample. Source rock samples can be layered giving "bedding" due to the burial process. The orientation of these layers can affect the AFM device measurement. With samples as layered (bedded), measurements may be made parallel and perpendicular to bedding.

At block 206, the method includes polishing the sample to decrease surface roughness. A sample surface may be polished mechanically and then finely polished via ion milling such as with an argon ion mill. The sample surface may be polished to reduce the surface roughness to less than 15 µm, or in the ranges of 1 nm to 15 µm, 1 nm to 13 µm, or 1 nm to 10 µm. In some implementations, imaging and the AFM SThM mode may be performed on the polished surface.

At block 208, the method includes calibrating the sensitivity, spring constant, and thermal circuit of the AFM cantilever. The method includes measuring the radius or diameter of the cantilever tip. In some implementations, the AFM cantilever is a silicon probe. The cantilever may have a metal film.

At block 210, the method includes creating a calibration curve with standards having known thermal conductivities. The standards may be material samples having known thermal conductivity.

At block 212, the method includes identifying a region of interest of the source-rock sample mounted on the sample holder. The region of interest may include organic compounds. The region may be identified as a region of interest via analysis of the source-rock sample. The region of interest of the source-rock sample may be identified via a reflected-light optical image, SEM, EDS, fluorescence, AFM-IR, or FTIR, or any combinations of these.

At block 214, the method includes selecting the set-point voltage for the AFM thermal conductivity measurement. The set-point voltage is linked to (correlative with) temperature of the AFM cantilever tip (tip portion).

At block 216, the method includes to null the electrical circuit associated with the voltage. For instance, the method includes measuring the heat flow to the environment or to a known standard material to zero the electrical circuit relative to the environment or the standard.

The tip may be moved from the sample surface to null. For heat flow to the environment as a reference, the method may include positioning the AFM at least five millimeters (or at least one centimeter) from the source-rock sample. In that case, the heat flow is from the tip to the environment of the AFM instrument and not to the source-rock sample. The heat flow may be determined or measured by the change in voltage difference across the tip heating element that maintains the tip at constant temperature (at temperature set point).

Heat may be energy with units of joules (J). Heat flow may be heat per time, such as in joules per second (J/s) or watts (W). Heat flux density may be the heat rate per unit area such as in watts per square meter (W/m$^2$).

At block 218, the method includes collecting SThM data and topography for a region of the sample at nano-resolution at a selected scan rate. The region may be the region of interest identified in block 212. The region may be a micro-region, for example, having a width in the range of 1 µm to 500 µm and a length in the range of 1 µm to 500 µm. The nano-resolution at which the data is collected may be, for example, at a resolution of 1 nm to 500 nm by 1 nm by 500 nm. In some implementations, the resolution is micro-resolution in microns, such as 2 µm to 5 µm by 2 µm to 5 µm.

In SThM, the AFM cantilever (probe) tip is rastered (in a scan pattern) along the sample surface while the AFM control loop for heating the tip measures the difference between the input voltage and the output voltage across the tip heating element. When the cantilever tip comes in contact with the sample in this first method of SThM, heat flows from the cantilever tip to the sample and the voltage difference is monitored. In implementations, the tip is not typically ramped in temperature but can be set at different temperatures for a series of scans.

At block 220, the method includes repeating SThM and topography scans at different scan rates if 3D effects are desired. The scan rate affects the contact time between the sample and the tip. With increased scan rate (moving slower), the measurement may generally be primarily affected by shallow regions of the sample. At decreased scan rate (moving slower), the deeper parts of the sample contribute to the response.

At block 222, the method includes checking diameter of the cantilever tip. The tip diameter or radius may be measured to determine if the tip diameter has changed due to wear or contamination. Tracking the tip diameter can account for the changing contact area on the sample due to change in tip diameter.

At block 224, the method includes repeating data collection for a range of micrometer regions and pixel sizes to cover domains of nanometer to millimeter sizes of the sample. The data collection may involve SThM and topography data. Different pixel sizes (or resolutions) may take the data from the measured tip region (for example, 10 nm by 10 nm) to produce an image at either the tip size resolution or lower resolution (up to several microns, such as 5 or 10 microns). The measurement may be converted to pixels as part of the technique. The number of pixels can be user selected and set independent of the scan lateral size. The number of pixels in a data set may be mode-specific. In some cases, the tip is constantly in contact with the sample and could be collecting more information than is converted to a pixel in the image. In other modes, the tip contacts the sample intermittently. In those modes, the regions in the tip deflection versus vertical distance may analyzed to obtain data for the images.

At block 226, the method includes repeating the process with samples mounted in varying orientations relative to bedding. The thermal conductivity may be measured at each position (for example, on the order at tens of nanometers) in one orientation of the sample relative to the AFM tip. To study anisotropy, additional samples from the same source rock may be mounted in different orientations relative to the AFM tip and the thermal conductivity additionally measured at each position along the sample as the AFM tip is rastered along the sample surface.

Additional source-rock samples may be collected, as in block 202. The method may include dismounting the initial source-rock sample. The additional source-rock samples may be cut to size and mounted to the AFM sample holder, as in block 204. The samples may be mounted sequentially with altered orientations relative to bedding of the sample. For each sample mounted, the actions of block 206 through block 224 may be repeated. The thermal conductivity of minerals and organic domains found in the source rock may be determined. Changes in the thermal conductivity may be linked to differences in the domain size, neighboring components, orientation, and thermal maturity.

In the second method (mentioned previously) of the SThM mode of operation, the AFM tip (coupled to the heat flow loop) can be maintained at a constant temperature. The constant temperature can be, for example, room temperature, ambient temperature, at least 25° C., at least 100° C., or up to the maximum heating temperature of the heating stage. The mounted source-rock sample is heated by a heating stage from the bottom of the sample. The AFM heating stage may be the AFM sample holder as a heater. The AFM heating stage may be a heating plate under the AFM sample holder. In implementations, the heating plate may be magnetized to hold the sample holder. In other implementations, the heating plate may have a recess to receive the sample holder provided generally that the recess not extend above the sample surface or interfere with the cantilever motion.

The heat that is transmitted through the mounted source-rock sample can then be detected by the AFM probe (cantilever) tip as a positive change in the voltage difference. This is different from the nanoTA mode and the aforementioned first method of the SThM mode because heat in the second method is supplied from the bottom of the sample.

In this second method of the SThM mode, the sample can be mounted in various orientations and on the heating stage. The temperature of the heating stage is set to change at a known rate as the sample is continuously scanned. In this case, the region of interest should be small enough that the time for the scan to complete is faster than for the temperature at the interrogated side of the sample to equilibrate. By scanning the sample, the SThM data collected indicates the time taken for heat transfer through the sample to be measured by the AFM cantilever. This SThM data can be linked to the mineralogy and lithology as measured by other spectral techniques, such EDS and SEM. An exemplary procedure for the second method utilizing SThM for source-rock analysis is given in FIG. 3.

Figure 3:
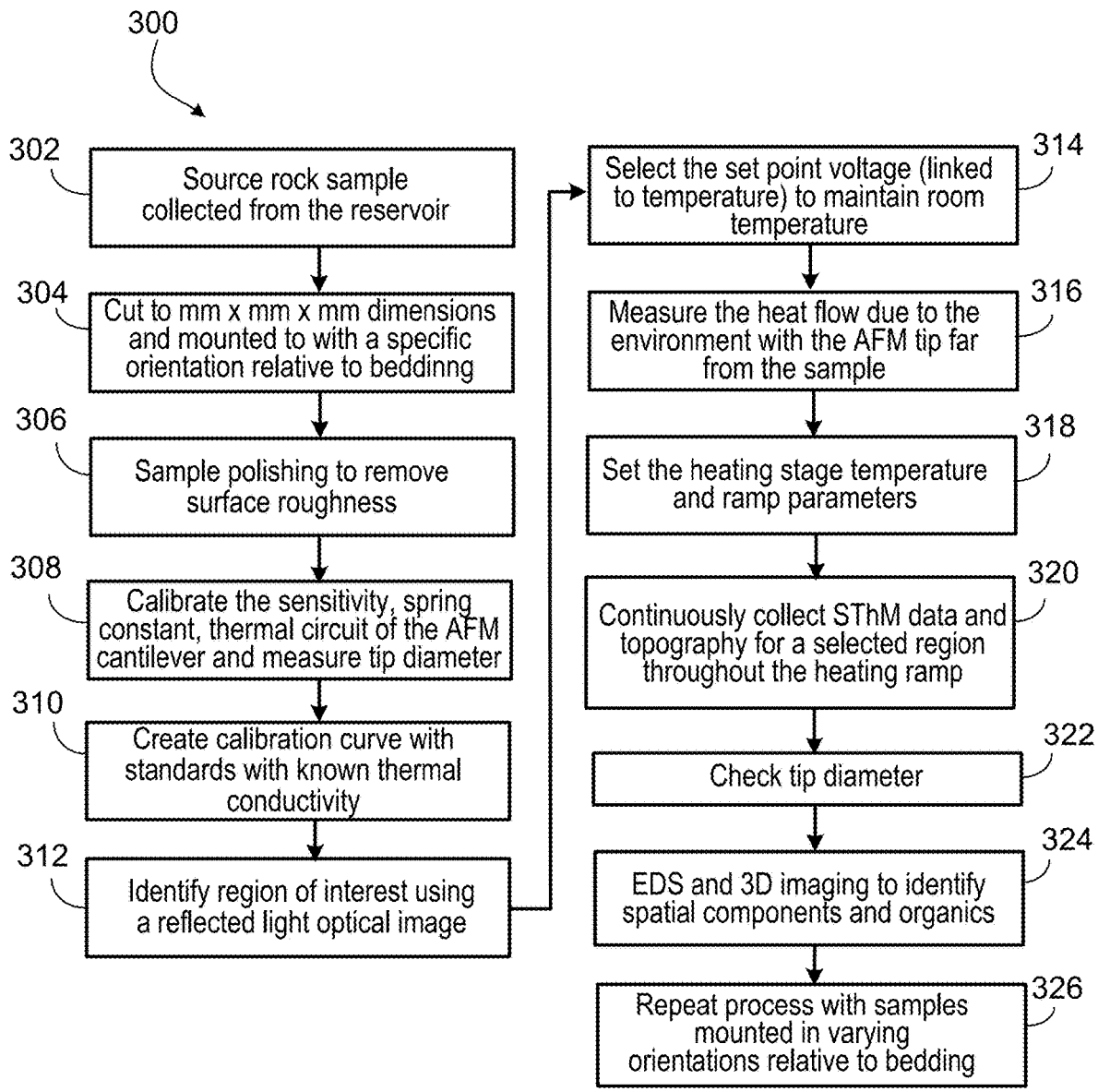
FIG. 3 is a block flow diagram of a method of scanning thermal microscopy of source rocks.

FIG. 3 is a method 300 of scanning thermal microscopy of source rocks. The method 300 includes the previously-discussed second method utilizing SThM for source-rock analysis. The method 300 includes a SThM procedure for source-rock analysis where the cantilever tip is a detection component but the heat is supplied from a controlled programmable heating stage. The method 300 involves detection with the AFM cantilever tip and heating through the mounted sample.

The method may determine thermal conductivity of the minerals and organic domains found in the source rock based upon how heat travels through the sample. The determined thermal conductivity may be linked to differences in 3D nanoscale variations in mineralogy, lithology, and organic content.

At block 302, the method includes collecting a rock sample from the geological formation reservoir. At block 304, the method includes shaping (cutting) the source-rock sample to millimeter dimensions, as previously discussed. The cut sample may be mounted to the AFM sample holder with a specific orientation relative to bedding in the sample. At block 306, the method includes polishing the sample to decrease surface roughness, as discussed.

At block 308, the method may include calibrating the AFM instrument. For example, the method may include calibrating a sensitivity of the AFM instrument, a spring constant of the AFM instrument, and a thermal circuit of a cantilever of the AFM instrument. The method includes measuring the diameter of the cantilever tip.

At block 310, the method includes creating a calibration curve with standards having known thermal conductivities. Calibration curves may be generated, for example, by measuring the change in voltage difference across the heating element on the AFM instrument cantilever tip when the tip interacts with the standards subjected to AFM thermal analysis via the AFM instrument. The calibration curve may also include measuring the known standards at the planned heating stage temperatures. There may be a different calibration curve for each standard at each planned experimental temperature.

At block 312, the method includes identifying a region of interest of the sample by analysis of the sample (for example, as mounted). The analysis may be via a reflected-light optical image, SEM, EDS, fluorescence, AFM-IR, or FTIR, or any combinations of these. In some implementations, an optical microscope of the AFM instrument may be employed to capture a reflected-light optical image of the sample.

At block 314, the method includes selecting the set-point voltage. The set-point voltage is linked to temperature. The set-point voltage may be selected to maintain the AFM tip at room temperature.

At block 316, the method includes zeroing the AFM tip heating circuit by measuring the heat flow from the AFM tip to the environment or to a reference material. The method may include measuring the heat flow to the environment with the AFM tip away from the mounted sample. For zeroing to the environment, the AFM tip may be maintained, for example, at least 1 mm distance from the mounted sample.

At block 318, the method includes setting the heat stage temperature and ramp parameters for heating the mounted sample. In some implementations, a set point for the heating stage temperature may be entered. The set point may be the desired temperature. The AFM instrument may display the actual temperature as the actual temperature increases to the set point temperature. The ramp parameters may include the rate of temperature increase per time, the amount of temperature increase per increment, and the amount of time per increment.

The heating stage temperature may generally be independent of the tip temperature. As indicated, the heating stage is heating the sample from the bottom while the tip may be held at a constant temperature (for example, voltage set point). The heating stage temperature can be changed while the tip temperature is held constant. The changing of heating stage temperature can be repeated at different tip temperatures if desired.

At block 320, the method includes collecting (for example, continuously) SThM data and topography for a selection region of the sample throughout the heating ramp. The resolution may be microscale or nanoscale. At block 322, the method includes checking tip diameter.

At block 324, the method may include employing EDS and 3D imaging to identify chemical components spatially. The chemical components may include organics. The organic and inorganic components may be identified spatially.

At block 326, the method includes repeating the process with samples mounted in varying orientations relative to bedding. Additional source-rock samples may be collected, as in block 302. The additional source-rock samples may be cut to size and mounted to the AFM sample holder, as in block 304. The samples may be mounted sequentially with altered orientations relative to bedding of the sample. For each sample mounted, the actions of block 306 through block 324 may be repeated. The thermal conductivity of the minerals and organic domains in the source rock may be determined based upon how heat travels through the sample and linked to nanoscale variations in mineralogy, lithology, and organic content.

EXAMPLES

The Examples are only given as examples and not meant to limit the present techniques. The Examples include Example 1 and Example 2. Each of the three source-rock samples was prepared for AFM measurements. Each sample was cut to desired dimension. The cut sample was mounted to a magnetic metal stub of an AFM sample holder and then polished to reduce the surface roughness.

Figure 4:
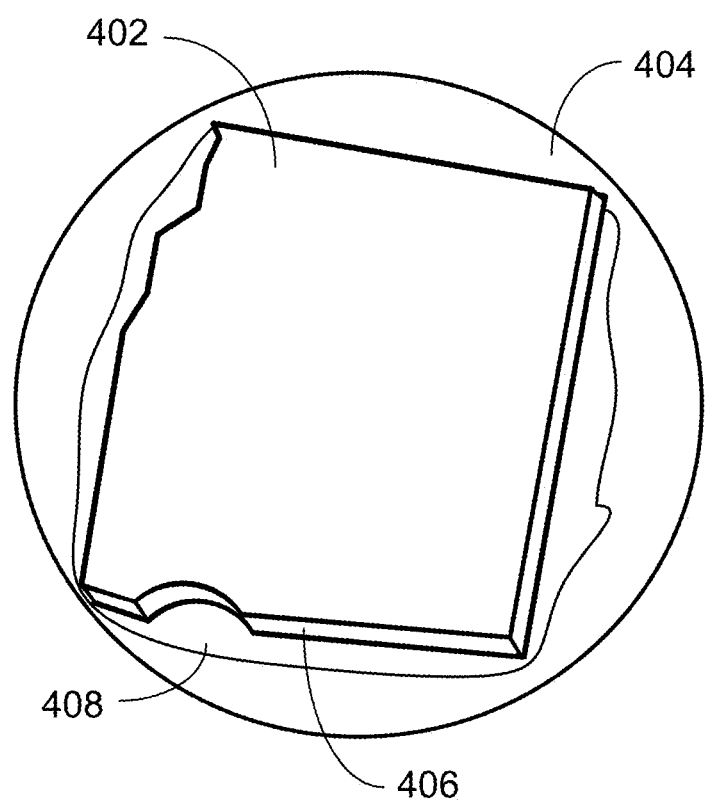
FIG. 4 is a diagram of a general representation of a prepared source-rock sample for AFM testing as in the Examples.

FIG. 4 is a general representation 400 of a prepared source-rock sample 402 for AFM testing as in the Examples. The top surface is polished. In the depicted implementation, the sample 402 is fixed to a sample holder 404. The sample 402 has a thickness 406. In some instances, a silver paste 408 may be deposited in selected locations around the perimeter of the sample to facilitate optional electrical measurements.

The three source-rock samples were from a shale formation having kerogen. Mineralogy for each sample was determined by performing powder x-ray diffraction (XRD) (see FIG. 5) on a Bruker D8 Advance Eco powder diffractometer (available from Bruker Corporation) and analyzing the diffraction peaks using Rietveld refinement. The Bruker Corporation headquarters is in Billerica, Mass., USA. Rietveld refinement characterizes crystalline materials in that neutron and x-ray diffraction of powder samples results in a pattern characterized by reflections (peaks in intensity) at certain positions. The mineralogy of each sample is shown in FIG. 5 (Table 500).

FIG. 5 is Table 500 giving mineralogy for each shale sample. The three shale samples are labeled as shale samples 1, 2, and 3, as indicated by reference numeral 502. The table gives values 504 in weight percent for the chemical components 506.

Rock-Eval® pyrolysis was utilized to determine the weight percent of organic matter and the thermal maturity (Table 1). Rock-Eval® pyrolysis may be performed to interpret thermal maturity or other properties. Rock-Eval® pyrolysis was developed by Institut Francais du Petrole (IFP) (French Institute of Petroleum) based at Rueil-Malmaison, France. In such a pyrolysis analysis, a rock sample undergoes increasing temperature in an inert atmosphere where three peaks of released hydrocarbons can be measured. The first peak (S1) represents the volatilization of any previously generated hydrocarbons present in the rock, given that the rock has reached thermal maturity. The second peak (S2) indicates the thermal degradation of any remaining organic material into hydrocarbons. The final peak (S3) is any organic $CO_2$ present in the rock. The temperature at which the S2 peak occurs may be an approximation of the thermal maturity of the rock. In addition to thermal maturation, pyrolysis peaks S1, S2, and S3 yield information about the type of organic material present in the rock.

In the Examples, crushed rock samples of about 60 milligrams (mg) each were subjected to a programmed temperature ramp where the organic matter thermally decomposed over time and the resulting by-products of this decomposition were measured via a flame ionization detector. During the pyrolysis analysis, a maximum temperature (Tmax) of complete combustion was reached and a pyrogram produced that recorded the hydrocarbon generative potential of the kerogen. The Tmax and the pyrogram can be utilized to define the maturity.

TABLE 1

Maturity and TOC data for each shale sample

| Shale Sample | S1 (mg/g) | S2 (mg/g) | S3 (mg/g) | PI | Tmax (° C.) | TOC (wt %) | HI | OI | H/C | Maturity |
|---|---|---|---|---|---|---|---|---|---|---|
| 1 | 0.01 | 0.03 | 0.15 | 0.13 | 608 | 1.63 | 2 | 0 | | Post |
| 2 | 2.18 | 27.76 | 0.07 | 0.07 | 420 | 6.46 | 430 | 7 | 1.250 | Immature |
| 3 | 1.21 | 1.93 | 0.39 | 0.39 | 452 | 3.87 | 50 | 7 | 0.645 | Late |

In Table 1, the three shale samples are labeled as shale samples 1, 2, and 3. Table 1 gives total organic content (TOC) in weight percent. Other properties in Table 1 are S1 (milligram per gram or mg/g), S2 (mg/g), S3 in (mg/g), (productivity index), Tmax (° C.), HI (hydrogen index), OI (oxygen index), and H/C (hydrogen to carbon ratio). S1, S2, and S3 are pyrolysis peaks. S1 is free hydrocarbons present in the sample before the analysis. S2 is the amount of hydrocarbons that formed during thermal pyrolysis of the sample (utilized to estimate the remaining hydrocarbon-generating potential of the sample). S3 is the $CO_2$ yield during thermal breakdown of kerogen.

The data provided in Table 500 (FIG. 5) and Table 1 are measured using common bulk methodologies where samples are crushed to perform the analyses. The common bulk methodologies did not provide spatial information about how the tabulated properties vary in intact rock.

While Rock-Eval® pyrolysis was employed in the Examples, present embodiments are not limited to Rock-Eval® pyrolysis. Other pyrolysis techniques and pyrolysis instruments are applicable. In general, a bulk pyrolysis instrument for analyzing source rock may be employed. The bulk pyrolysis instrument may include, for example, a Rock-Eval® pyrolysis instrument, the HAWK Pyrolysis Instrument from Wildcat Technologies (headquarters in Humble, Tex., USA), or the Source Rock Analyzer (SRA) from Weatherford International plc (headquarters in Baar, Switzerland).

Nanoscale thermal conductivity and nanoscale local thermal analysis were performed with a Bruker Dimension Icon AFM instrument using the Scanning Thermal Microscopy (SThM) and Nano Thermal Analysis (nanoTA) modules. The following examples demonstrate the application of SThM (Example 1) and nanoTA (Example 2) for source-rock samples.

Example 1

Figure 6:
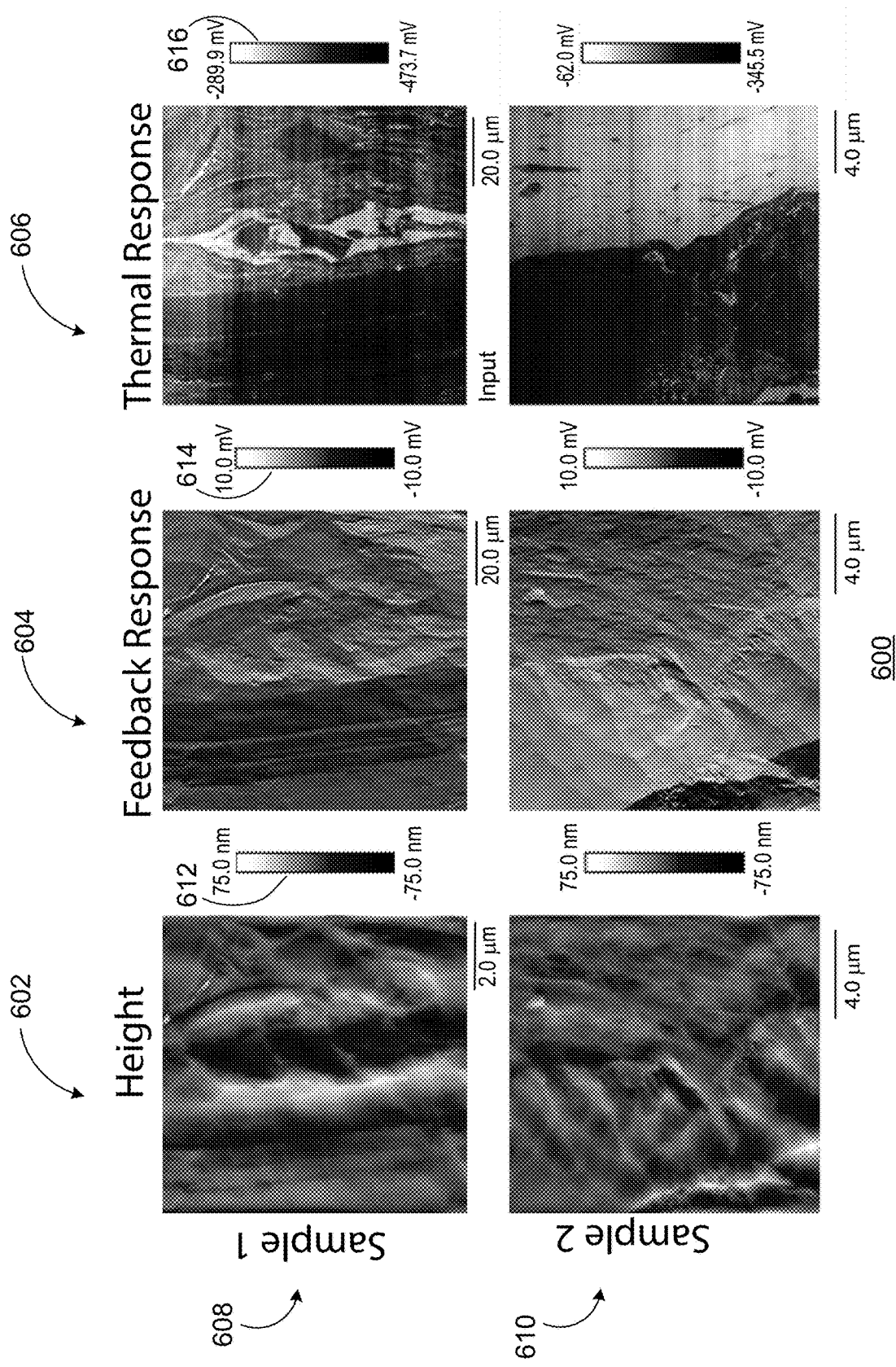
FIG. 6 is images associated with the analyses of the Samples 1 and 2 in the Example 1.

Shale Samples 1 and Sample 2 each of approximate dimensions 10 mm×10 mm×2 mm (see FIG. 4 for general representation) were oriented parallel to bedding. The Samples 1 and 2 were polished to nanometer smoothness employing Argon ion milling. AFM imaging and analysis were applied to the Samples 1 and 2. FIG. 6 gives images associated with SThM of source-rock Samples 1 and 2 showing topography or height (left), feedback response (center), and thermal response (right) for the two samples of different thermal maturity and mineralogy. Data demonstrate the ability to map difference in thermal conductivity (related to thermal response) for source rocks at the nanometer scale and demonstrate relative differences between samples.

FIG. 6 is images 600 associated with the analyses of Samples 1 and 2. Topography (height) image maps 602 on the left, feedback-response image maps 604 in the center, and thermal-response image maps 606 (right) are given for Sample 1 (608) and Sample 2 (610), respectively. The shading of the elevation or height legend 612 represents nanometers (nm). The shading of the feedback-response legend 614 represents millivolts (mV). The shading of the thermal-response legend 616 also represents mV.

Thus, FIG. 6 shows topography (600 left), feedback loop error (604 center), and thermal response (606 right) for each sample. The topography and feedback response data were flattened to remove sample tilt, detector variation, etc. and each type rescaled to the same scale for Example 1. Sample 1 data is a 10 um×10 um area scanned at 512×256 pixels providing a per pixel resolution of 20 nm×40 nm. The topography maps (with bright areas elevated and dark areas receded) of both Sample 1 and Sample 2 show a wavy texture indicative of the ion milling process but in general the two samples appear to be similar from the topography alone. The feedback loop error (or feedback response) incorporates the topography and mechanical response variation to provide qualitative comparisons between domains. The thermal response is related to the thermal conductivity of the materials.

Where the thermal response image shows a bright area (less negative), the voltage difference was lower meaning that the component of the source rock at that 20 nm×40 nm location drew less heat from the AFM tip and has low thermal conductivity. Areas that are dark had the opposite effect where less heat supplied by the AFM tip was drawn by the sample. In this way, the dark pixels are more thermally conductive than the light pixels.

The thermal response data shown in FIG. 6 is greater than 130,000 pixel measurements in each data set and provide a map of the thermal conductivity. The data provide the ability to observe the differences in thermal conductivity versus spatial and textural variations in the shale sample. When mineralogy maps are provided from EDS, these data can then be directly correlated to the minerals and organic components present at a resolution that is not possible by other techniques.

In addition to comparing nanoscale variations within one sample, response can be compared between samples. When comparing the thermal response (linked to thermal conductivity) of Sample 1 to Sample 2, Sample 1 appears to be more thermally conductive than Sample 2 (Sample 1 is more negative than Sample 2). In addition, with calibration, differences can be compared between the organic or clay domains as a function of thermal maturity. Sample 1 is post mature and Sample 2 is immature (see Table 1) and the organic domains in Sample 1 appear to be more thermally conductive than in Sample 2. This might indicate changes in the molecular structure with maturation.

Example 2

Figure 7:
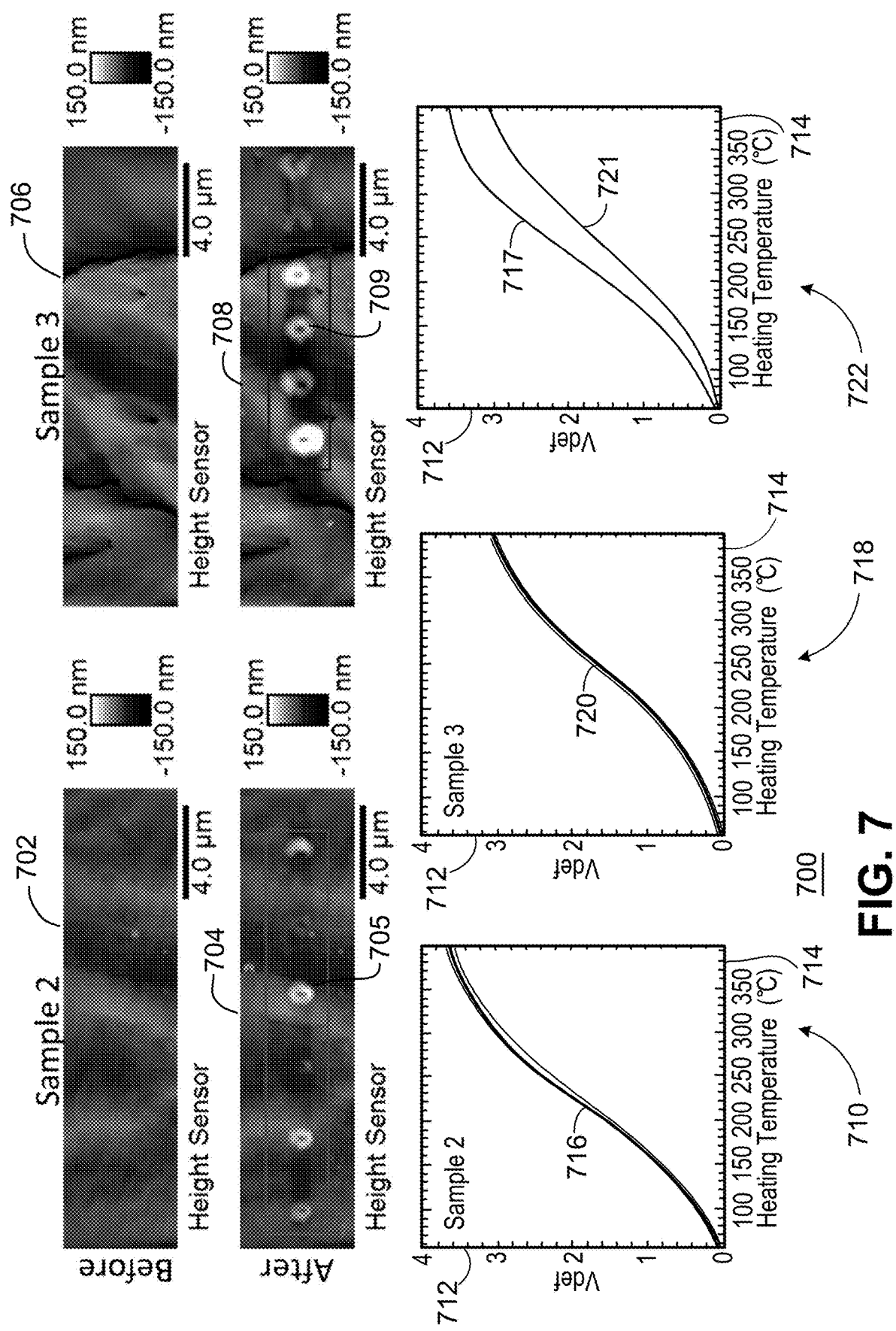
FIG. 7 is illustrations depicting results of the analyses of Samples 2 and 3 in Example 2.

Shale Samples 2 and 3 each having approximate dimensions of 10 mm×10 mm×2 mm (see FIG. 4 for general representation) were oriented parallel to bedding and polished to nanometer smoothness using Argon ion milling. FIG. 7 depicts results of nanoTA of source-rocks Samples 2 and 3 showing topography and height before and after heating (top) and deflection versus temperature data collected during the heating cycle (bottom). The data demonstrate the ability to measure the thermal expansion and permanent damage due to heating the sample at the nanoscale to micron scale. The behavior can be compared to thermal maturity.

FIG. 7 are illustrations 700 depicting results of the nanoTA analysis of Sample 2 and Sample 3 in Example 2. Image 702 is topography of Sample 2 before the nanoTA analysis (measurement). The image 702 was used to select areas to be measured for thermal response. Image 704 is topography of Sample 2 after the nanoTA analysis. Selected positions 705 for measurement have a deformation remaining after the measurement.

Image 706 is topography of Sample 3 before the nanoTA analysis (measurement). The image 706 was used to select areas (positions, points) to be measured for thermal response. Image 708 is topography of Sample 2 after the nanoTA analysis. Selected positions 709 for measurement have a deformation remaining after the measurement.

Plot 710 is AFM tip Vdef (nm) 712 versus tip temperature (° C.) 714 for Sample 2. Vdef 712 is the AFN device tip deflection in nanometers. The four curves 716 are for the four selected positions 705, respectively, as shown in image 704. Plot 718 is AFM tip deflection (nm) 712 versus tip temperature (° C.) 714 for Sample 3. The four curves 720 are for the four selected positions 708, respectively, as shown in image 708. Plot 722 is also AFM tip deflection (nm) 712 versus tip temperature (° C.) 714. The curve 717 is the average of the four curves 716 (for Sample 2) from plot 710. The curve 721 is the average of the four curves 720 (for Sample 3) from plot 718.

FIG. 7 shows topography before and after nanoTA data was collected for preselected positions in the organic matter in Sample 2 (left) (702, 704) and Sample 3 (right) (706, 708). Prior to the nanoTA measurement the topography (before) (images 702, 706) was used to select areas to be measured for thermal response. The after images 704, 708 show the permanent deformation (at 705, 709) remaining after the measurement at the locations measured. With calibration, the shape of these areas may provide information about the thermal response of the organic domains tested in this Example 2. The data plots 710, 718, 722 at the bottom portion of FIG. 7 show the deflection 712 versus tip temperature 714 for the selected positions of measurement. The left plot 710 is the four response curves 716 for the four selected positions 705, respectively, of Sample 2. The center plot 718 is the four response curves 720 for the four selected positions 709, respectively, of Sample 3. The plot 722 to the right shows a single curve 717 for the average response for Sample 2 and a single curve 721 for the average response for Sample 3.

These data indicate the thermal response of the sample during the thermal ramp and show that the less mature sample (Sample 2) expanded more than the more mature sample (Sample 3). The after images 704, 708 were collected after the heat element was removed from the sample. The raised edges surrounding the heat spot are less raised for Sample 2 than for Sample 3. This may indicate that the response of Sample 2 is more reversible than that of Sample 3, which may be because of (or linked to) thermal maturity and crosslink density.

Figure 8:
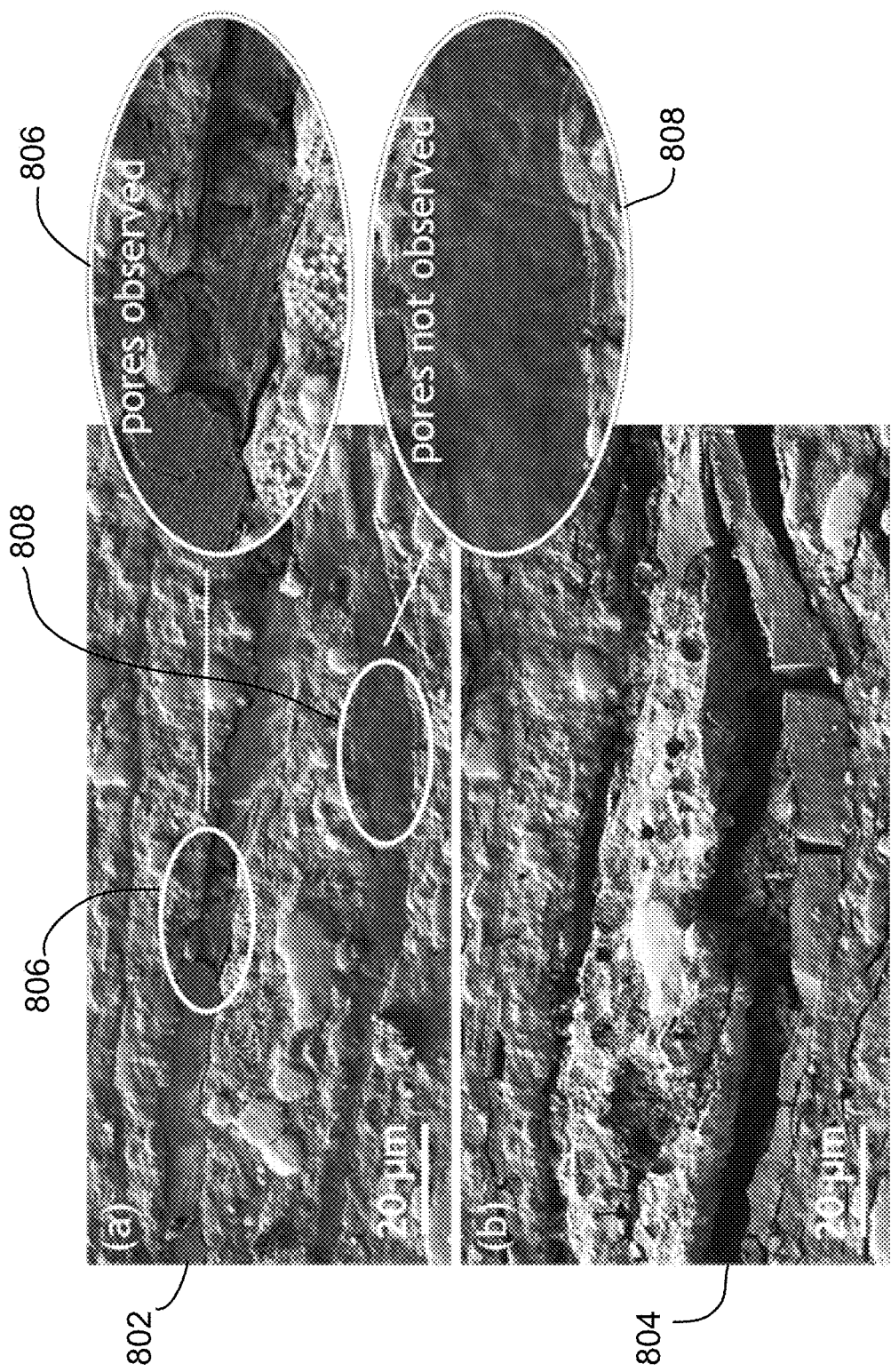
FIG. 8 is scanning electron microscope (SEM) images of a source-rock sample.

To illustrate how thermal conductivity measurements using AFM can aid in source-rock studies, SEM images of a source-rock (shale) sample are shown in FIG. 8. FIG. 8 gives an SEM image 802 of source-rock shale captured (a) before oxidative fluid treatment. The SEM image 804 is the source-rock shale (b) after oxidative fluid treatment. The insets to the right are enlarged images of the areas 806, 808 circled within image 802 which is before oxidative fluid treatment.

Thus, FIG. 8 is SEM images 800 of a source-rock sample. The source-rock sample was cut to mm dimensions, mechanically polished, and imaged via SEM. The SEM image 802 is an area of the sample where two veins of organic matter run horizontally across the sample. Areas 806, 808 of the sample are enlarged to show developed porosity (upper vein) and no visible pores (lower vein). Due to the resolution of the SEM (greater than 10 nm), it is possible that pores are also developed in the lower vein of kerogen though their size is less than 10 nm. Scanning thermal AFM measurements may provide insight into whether pores are present in this region of the lower vein. Further, nanothermal AFM measurements may indicate whether these organic domains contain only kerogen or also contain bitumen or pyrobitumen.

The sample was subjected to oxidative treatment and then reimaged in the same area via SEM as shown in SEM image 804. The entire upper vein of organic matter was removed from the source rock. A majority of the lower vein remained. The less reactivity exhibited by the lower vein may be the result of bitumen or pyrobitumen, or both. Alternatively, this less reactivity may be related to the less surface area of the substrate in contact with the fluid due to lack of pore development. By capturing thermal conductivity information from AFM and linking such data to the chemical and physical structure of the organic matter, a better assessment of the fluid effects and potential effectiveness in the field can be performed.

Present embodiments are a method to measure thermal conductivity and material transitions at resolution less than 100 nm per pixel and map these properties in source rock and shale. This includes the ability to measure these properties for the individual inorganic and organic components of these materials in intact rock which is not possible with lower resolution techniques. Traditional techniques to measure thermal conductivity and transition temperatures on geologic samples are bulk measurements and provide the properties of the composite (not the individual components).

Certain embodiments employ measurements of nanoscale thermal conductivity and nanoscale thermal expansion to: (1) distinguish kerogen, bitumen, and pyrobitumen; (2) determine a correlation between thermal conductivity and porosity in kerogen; (3) understand porosity development at the nanoscale; (4) link nanoscale thermal alteration to polymeric properties of the organic domains; (5) observe thermal conductivity versus grain size and rock texture (effects of scattering domains); and (6) determine relative differences in thermal conductivity to distinguish less mature from more mature source rocks. Some embodiments rely on thermal conductivities captured by AFM methods to predict and diagnose well performance. Such may include to: (1) understand local heating effects of fracturing fluid or organic matter and timescale for reaching activation temperature of reactions; (2) utilize physical (porosity) or chemical (kerogen versus bitumen) information from thermal AFM to understand reactivity of source-rock organic components and predict or diagnose fracturing fluid stimulation treatment; and (3) link thermal conductivity of source rock to fracture propagation in the case where organic matter is degraded on the timescale of the treatment. Embodiments may consider the nanocomposite nature of kerogen-rich source rocks, employ AFM to measure the effects of orientation, and capture differences in thermal conductivity for amorphous versus ordered material. Some embodiments may accommodate geochemical consideration, distinguish diagenetic minerals from authigenic minerals, and apply to basin modeling.

Figure 9:
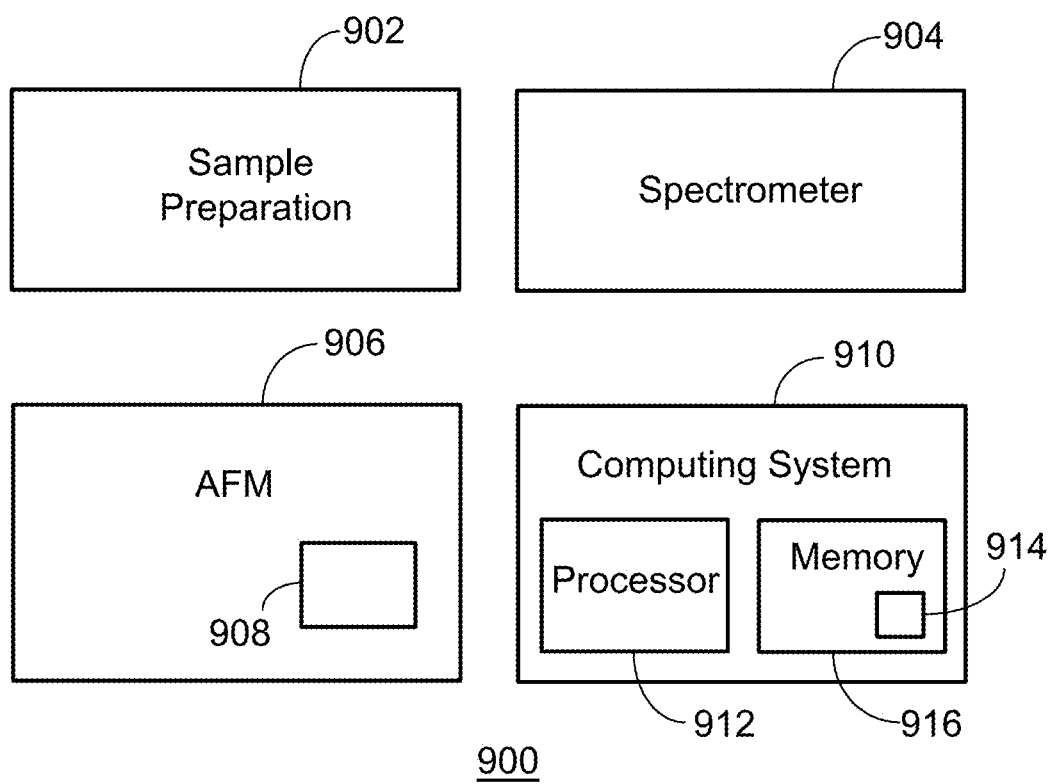
FIG. 9 is a diagram of a source-rock evaluation system to analyze a source-rock sample.

FIG. 9 is a source-rock evaluation system 900 to analyze a source-rock sample and correlate sample analyses to the rock formation from which the source-rock sample was collected. The rock formation may be a geological formation characterized as an unconventional formation. The rock formation may have hydrocarbons such as crude oil and natural gas. In some implementations, the rock formation is a shale formation.

A sample preparation system 902 may receive source-rock sample material collected from the rock formation. The sample preparation system 902 may include tool(s) to cut or otherwise shape the source-rock sample material into a source-rock sample for analysis. The source-rock sample as shaped or cut may be mounted to a sample holder of an AFM instrument. In addition, the preparation system 902 may include refining devices to polish one or more surfaces of the source-rock sample. For instance, a mechanical polisher may achieve gross or coarse polishing of the source-rock sample surface. An ion mill (for example, argon ion mill) may achieve fine polishing of the source-rock sample surface. In particular implementations, the surface may be polished to a specified surface roughness, such as in a range of 1 nm (or less) to 13 µm. In some implementations, a top surface of the source-rock sample is polished for receipt of (or interaction by) an AFM probe (cantilever) and for imaging.

In the illustrated embodiment, the source-rock evaluation system 900 may include a spectrometer 904 system to analyze the source-rock sample including the prepared source-rock sample. The spectrometer 904 system may measure or identify chemical components or constituents of the source-rock sample, such as organic compounds (for example, kerogen and bitumen) and inorganic compounds (for example, minerals, and clay). In certain implementations, the spectrometer 904 system is an EDS instrument having circuitry (including a hardware processor and memory) and a user-interface. In some implementations, the spectrometer 904 may be at least one of an AFM-infrared red spectroscopy (AFM-IR) instrument, a micro-Fourier-transform infrared spectroscopy (micro-FTIR) instrument, or a fluorescence spectroscopy instrument. Imaging of the source-rock sample may be performed, for example, via a microscope associated with or separate from the spectrometer 904 system. Such microscopic imaging may facilitate identifying the chemical components spatially on the source-rock sample including at the microscale or nanoscale.

The source-rock evaluation system 900 includes an AFM instrument 906 (system) that may employ scanning microscopy to analyze the source-rock sample at the microscale or nanoscale. In the Examples presented earlier, the AFM instrument employed was Bruker Dimension Icon AFM instrument using the SThM and nanoTA modules.

The AFM instrument 906 employs scanning probe microscopy that is atomic force microscopy. The AFM instrument 906 takes measurements of the source-rock sample. The measurements may be thermal property measurements, such as thermal conductivity or material transition temperature. The AFM instrument 906 may analyze and image the polished surface of the source-rock sample prepared for the AFM. The AFM instrument 906 may be operated in nanoTA mode or SThM mode, as discussed earlier. The AFM instrument 906 may include circuitry 908 that provides for a user interface and for selection of different operating modes of the AFM instrument 906. In certain embodiments, the AFM instrument 906 may perform microscopic imaging on the source-rock sample at microscale or nanoscale, such as on the polished surface of the source-rock sample. In some embodiments, this imaging (for example, optical imaging) may be performed contemporaneous with the AFM instrument 906 measuring thermal conductivity.

For nanoTA, the AFM instrument 906 includes a temperature controller such as a thermal applications controller (TAC). The temperature controller and a heating element (for example, metal film or resister on cantilever tip portion) may heat and control the temperature of the AFM instrument probe (cantilever) tip. The heating element may be a circuit printed on the AFM cantilever that heats the tip, as with the AFM device employed in the Examples.

In nanoTA, heat is transferred from the probe tip to the mounted source-rock sample. In some approaches of SThM as a mode of operation, the AFM cantilever tip is similarly heated. The AFM tip is rastered along the sample surface while an AFM control loop for heating the tip measures the difference between the input voltage and the output voltage across the heating element. When the tip is away from the sample, the voltage difference is related to heat loss due to ambient conditions. When the tip comes in contact with the sample, heat flows from the tip to the sample and the voltage difference is monitored.

Other approaches for the SThM mode involves detection with the AFM cantilever tip and heating through the mounted sample. The temperature of the AFM cantilever temperature may be maintained constant, for example, at room temperature. The temperature of the heating stage is set to change at a known rate as the mounted source-rock sample is scanned. The mounted source-rock sample heated by a heating stage from the bottom of the sample. The AFM heating stage may be the AFM sample holder as a heater. The AFM heating stage may be a heating plate under the AFM sample holder.

The AFM instrument 906 (and the spectrometer 904 if employed) can have a computing processor and memory storing code executed by the processor for operation of the instrument. The code may include data-interpretation logic or instructions to convert the directly read data to output data based on the equipment. The executed code may generally provide for a user interface. The instrument memory can typically store data. The computing processor as directed by the executed code may act as a controller to generally run the AFM instrument 906 including to instruct the AFM instrument 906 how to move the cantilever tip and where to find the mounted sample. The controller may take the real-time data from the AFM instrument tip motion or heat measurement and converts the data to topography, adhesion properties, mechanical properties, and maps of properties.

The source-rock evaluation system 900 may also include a computing system 910 for data analysis and data correlations. The computing system 910 can be local, remote, or portable. The computing system 910 has a processor 912 and memory 914 storing code 916 (for example, logic and instructions) executed by the processor 912 to perform aforementioned actions related to the present techniques. The computing system 910 may be single computing device or a computer, a server, a desktop, a laptop, multiple computing devices or nodes, a distributed computing system, or control system. The computing system 910 may be local (for example, in the laboratory) or remote from the spectrometer system 904 and AFM instrument 906 system. The computing system 910 may represent multiple computing systems or devices across separate geographical locations. The computing system 910 may be a component of a control system. The processor 912 may be one or more processors, and each processor may have one or more cores. The hardware processor(s) 712 may include a microprocessor, a central processing unit (CPU), graphic processing unit (GPU), or control card. The memory 914 may include volatile memory (for example, cache and random access memory or RAM), nonvolatile memory (for example, hard drive, solid-state drive, and read-only memory or ROM), and firmware.

The computing system 910 may store calibration equations or calibration curves (for example, as generated in block 110 of FIG. 1 and block 210 of FIG. 2). In operation, the computing system 910 may receive input of responses of the cantilever tip in the AFM instrument 906 analysis of a mounted actual sample. The input to the computing system 910 may be automated or manual (user input). The computing system 910 may determine or calculate the relevant thermal property (for example, thermal conductivity or transition temperature) based on the received inputs and the applicable calibration curve.

The computing system 910 is unconventional, for example, in that the computer facilitates determination thermal properties of a source-rock sample at microscale or nanoscale. In this context, the computer is innovative with respect to feasibility and accuracy. The technology of geological formation evaluation (including evaluation of unconventional formations or shale formations) is improved. The technology areas of basin modeling and well production performance analysis are advanced.

Figure 10:
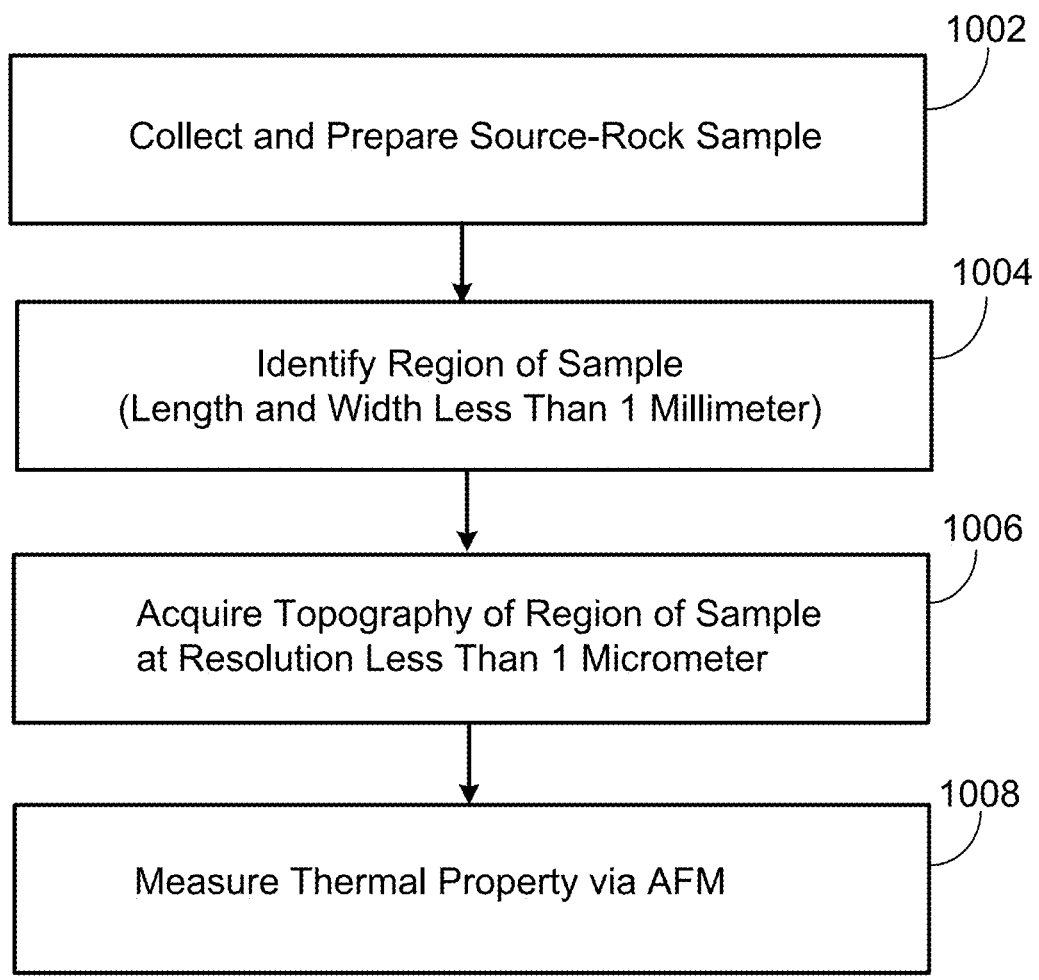
FIG. 10 is a block flow diagram of a method of evaluating a geological formation.

FIG. 10 is a method 1000 of evaluating a geological formation which may be an unconventional formation (for example, a shale formation). The formation may have hydrocarbons. The hydrocarbons may be crude oil or natural gas. The formation may have inorganic components (minerals) and organic components (for example, kerogen). In regions of the formation, the organic components may be intertwined with the inorganic components. The geological formation may be labeled a rock formation, a source rock formation, a hydrocarbon-containing formation, a reservoir, a hydrocarbon reservoir, and a source rock reservoir.

At block 1002, the method includes collecting and preparing a source-rock sample. The source-rock sample may be collected from the geological formation (source-rock formation). The sample preparation may include forming (for example, cutting or shaping) the source-rock sample. The shaped or cut source-rock sample may be mounted to an AFM sample holder. In implementations for AFM SThM, the source-rock sample may be mounted to the sample holder with a specified orientation relative to bedding of the source-rock sample.

The sample preparation may include polishing the source-rock sample to reduce surface roughness. If polishing is employed, the polishing may include mechanical polishing and ion milling (for example, argon ion milling) the surface to a specified surface roughness. In one implementation, the specified surface roughness is in a range of 1 nm to 13 µm. In another implementation, the surface roughness in less than 15 µm.

At block 1004, the method includes identifying a region or region of interest on the sample. In certain implementations, the region has dimensions less than 1 mm. The length and width of the region may each be less than 1 mm. In some implementations, the region of interest may be identified via a reflected-light optical image of the source-rock sample. In some cases, spectrometer data can be combined with the optical image to locate regions. In addition to or in lieu of a reflected-light optical image, the region of interest may be identified via SEM, EDS, fluorescence, AFM-IR, or FTIR, or any combinations of these. In implementations for AFM nanoTA, the method may include selecting measurement areas or points of the region based on a topography map and the presence of organic domains.

At block 1006, the method include acquiring topography of the region of the sample, for example, at a resolution less than 1 micrometer. In certain embodiments, the AFM instrument in contact mode is utilized. In contact mode, the AFM cantilever tip moves along the sample surface and the deflection of the cantilever is measured to produce a topography map. A topography map of the micrometer region may be acquired at nanometer resolution. In AFM SThM, topography of the region may be acquired during the heating of the cantilever tip or the source-rock sample and during collecting of SThM data.

At block 1008, the method includes measuring, via AFM, a thermal property of the source-rock sample a scale less than 1 millimeter. In AFM SThM, the thermal property may be thermal conductivity. In AFM nanoTA, the thermal property may be material transition temperatures (Tg or Tm) or thermal indicators of chemical composition and crosslink density. The AFM in nanoTA mode may measure thermal expansion as an indicator of chemical composition or crosslink density.

Thermal expansion may refer to a fractional change in size of a material in response to a change in temperature. The fractional change can be linear expansion, areal expansion (or superficial expansion), or linear expansion (or cubical expansion) and can be directly proportional to temperature change ($\Delta T$). A coefficient of thermal expansion may be the ratio of the fractional change in size of a material to its change in temperature and can have units of the inverse of kelvin (1/K).

In AFM nanoTA, the measurement may be at the measurement areas selected based on the topographical map and the presence of organic domains. NanoTA data may be collected at each measurement area over a ramp of the AFM instrument probe tip temperature from a first temperature (for example, room temperature) to a second temperature (for example, less than 500° C.). The method may include determining material differences in organic domains based on temperature-vs-deflection data collected by the AFM instrument.

The method may include measuring thermal conductivity of the region by the AFM instrument in SThM mode at a resolution less than 1 micrometer and at a selected scan rate. In the AFM SThM mode, the method may include selecting a set-point voltage for heating the AFM instrument cantilever or cantilever tip for measuring the thermal conductivity of the region. The voltage response associated with the heat transfer between the cantilever tip and the mounted sample may be correlative with thermal conductivity of the mounted sample.

A first approach of the SThM mode is to set the temperature of the AFM instrument cantilever tip (via a heat ramp) during the scan while not heating the sample and in which heat transfers from the tip to the mounted sample. The tip may be set to a temperature greater than room temperature. The scan and collecting of SThM data can occur during the heat ramp.

A second approach is to maintain the cantilever tip at a constant temperature (for example, room temperature) and set the temperature of the mounted sample at a temperature via a heating stage below the sample. Heat may transfer from the sample to the tip. Implementations can include holding constant the sample temperature while initially scanning at a first temperature of the tip and then scanning at a second temperature of the tip. Scans may be performed at a series of different temperatures of the tip while the sample temperature is held constant. This could similarly be performed where the tip temperature is held constant and a heating stage changes the sample temperature over a series of different temperatures during scans. For the heating stage cases, these scans could be performed while the sample is coming to temperature equilibrium (set point) or after the sample has reached temperature equilibrium.

The method may include collecting SThM data and topography for the region at the resolution less than 1 millimeter for multiple different scan rates to give three dimensional (3D) effects. The method may include repeating the SThM process with source-rock samples mounted in the AFM sample holder in varying orientations relative to bedding of the source-rock samples. The thermal conductivity of the minerals and organic domains in the source rock may be determined based upon how heat travels through the samples and linked to nanoscale variations in mineralogy, lithology, and organic content. The method may also include employing EDS and 3D imaging to identify chemical components spatially.

The method may include utilizing a bulk pyrolysis instrument for analyzing source rock to interpret thermal maturity. The pyrolysis may be the decomposition of organic matter by heating in the absence of oxygen. The pyrolysis may be employed to measure richness and maturity of potential source rocks. In a pyrolysis analysis, the organic content may be pyrolyzed in the absence of oxygen and then combusted. The amount of hydrocarbons and carbon dioxide released may be measured. Implementations of the bulk pyrolysis instrument include, for example, the HAWK Pyrolysis Instrument, the Source Rock Analyzer (SRA), and Rock-Eval® pyrolysis instrument. In the pyrolysis, a sample may be progressively heated (for example, to 550° C.) under an inert atmosphere. During the analysis, the hydrocarbons already present in the sample are volatized and the amount of these hydrocarbons measured and recorded as a peak known as S1. Next, the amount of hydrocarbons generated by pyrolysis of kerogen in the sample is recorded as an S2 peak. The amount of $CO_2$ generated is recorded as the S3 peak. The amount of residual carbon is measured and recorded as S4. The percent total organic carbon (TOC) may be related to the S peaks.

An embodiment is a method of evaluating a geological formation including preparing a source-rock sample from the geological formation and acquiring a topography map of a region of the source-rock sample at a resolution less than 1 µm. The region may be chosen as a region of interest identified based on a reflected-light optical image of the source-rock sample including evaluating gray scale, color variation, domain shape, or features adjacent the region, or any combinations of these. Measurement areas of the region are selected based on the topography map. A portion of interest of the region may be identified based on the topography map. The portion of interest may include organic domains or inorganic domains, or both, of the rock structure. The measurement areas of the region may be selected based on the portion of interest and on the topography map.

The method includes determining, via AFM, thermal conductivity of the source-rock sample at the measurement areas at a scale less than 1 millimeter. In implementations, the measurement areas each have a width in a range of 10 µm to 500 µm and a length in a range of 10 µm to 500 µm. The AFM may involve scanning thermal microscopy (SThM), such as with the AFM instrument in SThM mode. The determining of the thermal conductivity via AFM may involve applying voltage to a cantilever tip portion of a cantilever of the AFM instrument utilized to determine the thermal conductivity. The applying of voltage to the cantilever tip portion may include applying voltage to a heating element on the cantilever tip portion. In implementations, the heating element is a circuit printed on the cantilever. The determining of thermal conductivity may involve measuring voltage difference across the heating element (for example, across the circuit printed on the cantilever). In certain implementations, the method includes maintaining the cantilever tip portion at a set-point temperature. The determining of the thermal conductivity may involve transferring heat from the cantilever tip portion to the source-rock sample. On the other hand, the determining of the thermal conductivity may involve heating the source-rock sample and transferring heat from the source-rock sample to the cantilever tip portion. The determination of the thermal conductivity of the source-rock sample via AFM may include measuring a voltage difference across heating element (for example, across the circuit printed on the cantilever tip portion) while the cantilever tip portion is interacting with the source-rock sample.

The method may include generating a calibration curve based on standards samples each having a known thermal conductivity. The calibration curve may relate voltage difference across the heating element on the cantilever tip portion with values of thermal conductivity. The calibration curve may be generated by measuring voltage difference across the heating element and with the cantilever tip portion interacting with the standards samples. The determination of the thermal conductivity of the source-rock sample via AFM may involve utilizing the calibration curve. For instance, the calibration curve may be utilized to convert a measured voltage difference to a thermal conductivity value based on the calibration curve. The determination of the thermal conductivity of the source-rock sample via AFM may include correlating the measured voltage difference with a value of thermal conductivity indicated by the calibration curve. The measurement of the voltage difference may include measuring a change in voltage difference.

Another embodiment is a method of evaluating a geological formation. The method includes mounting a source-rock sample from the geological formation to a sample holder of an AFM instrument. The source-rock sample may be mounted with a specified orientation relative to bedding of the source-rock sample. The method includes identifying a region of interest of the source-rock sample via a reflected-light optical image of the source-rock sample. In addition to or in lieu of a reflected-light optical image, the region (as a region of interest) may be identified in certain embodiments via SEM, EDS, fluorescence, AFM-IR, or FTIR. The method includes determining thermal conductivity of the region with the AFM instrument in SThM mode. The AFM instrument employs a cantilever having a cantilever tip. The determination of thermal conductivity may include transferring heat from the cantilever tip to the source-rock sample mounted in the sample holder. The determination of the thermal conductivity may involve collecting SThM data for the region at a resolution less than 1 micrometer at a selected scan rate, and where the region comprises a width and length each less than 1 millimeter. The method may include collecting topography of the region at the resolution at the selected scan rate. The selected scan rate may include multiple different scan rates to give three dimensional (3D) effects.

The method may include determining indication of heat flow from the cantilever tip to a known material standard. The method may include determining indication of heat flow from the cantilever tip to an environment of the AFM instrument at least 1 millimeter (mm) from the mounted source-rock sample.

The method may include maintaining the cantilever tip at a constant temperature (for example, room temperature). The method may include setting temperature and ramp parameters of a heating stage of the AFM instrument to heat the source-rock sample. The heating stage provides a heating ramp during the determining of thermal conductivity. The method may involve collecting SThM data and topography for the region at a resolution less than 1 millimeter through the heating ramp. The method may include checking diameter or width of the cantilever tip. In certain implementations, the diameter is in a range of 10 nm to 100 nm.

Yet another embodiment is a method of evaluating a geological formation. The method includes preparing a source-rock sample from the geological formation and acquiring a topography map of a region of the source-rock sample at a resolution less than 1 µm. The region may be chosen as a region of interest identified based on a reflected-light optical image of the source-rock sample. Alternatives to a reflected-light optical image include SEM, EDS, fluorescence, AFM-IR, or FTIR, or any combinations of these. The method includes selecting measurement areas of the region based on the topography map. In implementations, the measurement areas may each have a width in a range of 10 µm to 500 µm and a length in a range of 10 µm to 500 µm. The method may include identifying organic domains of the region based on the topography map. The measurement areas of the region may be selected based on the organic domains and on the topography map.

The method includes determining material transition temperature of the source-rock sample at the measurement areas at a scale less than 1 millimeter via AFM with an AFM instrument. The material transition temperature may be glass transition temperature (Tg) or melting point temperature (Tm). The method may also include determining thermal expansion or crosslink density of the source-rock sample at the measurement areas at the scale less than 1 millimeter via the AFM instrument. The AFM may involve nanoTA. The AFM instrument may be in nanoTA mode. The AFM instrument includes cantilever having a cantilever tip. The method may include sensing deflection of the cantilever as affected by interaction of the cantilever tip with a surface of the source-rock sample. A voltage may be applied to the cantilever tip. The determining of the material transition temperature may involve collecting nanoTA data at each measurement area over a temperature ramp of the cantilever tip from a first temperature to a second temperature. The first temperature may be, for example, room temperature. The second temperature may be, for example, less than 500° C. The nanoTA data may include deflection of the cantilever versus temperature of the cantilever tip. The deflection is in response to contact of the cantilever tip with the sample. The method may include performing a topography scan and measuring height, indention, and lateral extent of thermal damage of the region caused by collecting the nanoTA data. The method may include determining material differences in organic domains in the measurement areas based on deflection of the cantilever tip versus temperature of the cantilever tip. The method may include generating a calibration curve with the AFM instrument by measuring material transition temperature of standards samples each having a known material transition temperature.

Yet another embodiment is a method of evaluating a geological formation. The method includes mounting a source-rock sample from the geological formation to a sample holder of an AFM instrument. The source-rock sample is mounted with a specified orientation relative to bedding of the source-rock sample. The method includes identifying a region of interest of the source-rock sample via a reflected-light optical image, SEM, EDS, fluorescence, AFM-IR, or FTIR of the source-rock sample. In implementations, the region may have a width and length each less than 1 millimeter. The method includes determining a material property of organic domains of the region via the AFM instrument in nanoTA mode. The material property may be Tg, Tm, crosslink density, thermal expansion, or thermal damage. The material property may be determined by collecting nanoTA data for the region at a resolution less than 1 micrometer at a selected ramp rate for temperature of the source-rock sample. The method may include collecting topography of the region at the resolution. The method may include checking diameter of a cantilever tip of the AFM instrument.

A number of implementations have been described. Nevertheless, it will be understood that various modifications may be made without departing from the spirit and scope of the disclosure.

What is claimed is:

1. A method of evaluating a geological formation, comprising:
    preparing a source-rock sample from the geological formation;
    acquiring a topography map of a region of the source-rock sample at a resolution less than 1 micrometer (μm);
    choosing the region as a region of interest identified based on a reflected-light optical image of the source-rock sample;
    selecting measurement areas of the region based on the topography map; and
    determining, via atomic force microscopy (AFM), a thermal conductivity of the source-rock sample at the measurement areas at a scale less than 1 millimeter.

2. The method of claim 1, wherein the measurement areas each comprise a width in a range of 10 μm to 500 μm and a length in a range of 10 μm to 500 μm.

3. The method of claim 1, wherein choosing the region as a region of interest identified based on a reflected-light optical image comprises evaluating gray scale, color variation, domain shape, or features adjacent the region, or any combinations thereof.

4. The method of claim 1, comprising selecting the region as a region of interest identified based on an analysis of the source-rock sample, the analysis comprising scanning electron microscopy (SEM), energy dispersive spectroscopy (EDS), fluorescence, AFM-infrared red (IR), or Fourier-transform infrared spectroscopy (FTIR), or any combinations thereof.

5. The method of claim 1, comprising identifying a portion of interest of the region based on the topography map, wherein the selecting comprises selecting measurement areas of the region based on the portion of interest and on the topography map, and wherein the portion of interest comprises organic domains or inorganic domains, or both, of a rock structure of the source-rock sample.

6. The method of claim 1, wherein the AFM comprises scanning thermal microscopy (SThM).

7. The method of claim 1, wherein determining the thermal conductivity via AFM comprises determining the thermal conductivity with an AFM instrument in a scanning thermal microscopy (SThM) mode.

8. The method of claim 1, wherein determining the thermal conductivity via AFM comprises applying a voltage to a cantilever tip portion of a cantilever of an AFM instrument utilized to determine the thermal conductivity.

9. The method of claim 8, comprising maintaining the cantilever tip portion at a set-point temperature, wherein determining the thermal conductivity comprises transferring heat from the cantilever tip portion to the source-rock sample.

10. The method of claim 8, wherein determining the thermal conductivity comprises heating the source-rock sample and transferring heat from the source-rock sample to the cantilever tip portion.

11. The method of claim 8, wherein determining the thermal conductivity comprises measuring a diameter of the cantilever tip portion, wherein the diameter is in a range of 10 nm to 100 nm.

12. The method of claim 8, wherein applying voltage to the cantilever tip portion comprises applying the voltage to a heating element on the cantilever tip portion.

13. The method of claim 12, wherein the heating element comprises a circuit printed on the cantilever.

14. The method of claim 13, wherein determining the thermal conductivity comprises measuring a voltage difference across the circuit printed on the cantilever.

15. A method of evaluating a geological formation, comprising:
    preparing a source-rock sample from the geological formation;
    acquiring a topography map of a region of the source-rock sample at a resolution less than 1 micrometer (μm);
    selecting measurement areas of the region based on the topography map;
    generating a calibration curve based on standards samples each having a known thermal conductivity; and
    determining, via atomic force microscopy (AFM), a thermal conductivity of the source-rock sample at the measurement areas at a scale less than 1 millimeter, wherein determining via AFM the thermal conductivity of the source-rock sample comprises utilizing the calibration curve.

16. The method of claim 15, wherein the calibration curve relates a voltage difference across a heating element of a cantilever tip portion of an AFM instrument with values of the thermal conductivity.

17. The method of claim 16, wherein the heating element comprises a circuit printed on the cantilever tip portion, and wherein determining via AFM the thermal conductivity of the source-rock sample comprises measuring a voltage difference across the circuit printed on the cantilever tip portion while the cantilever tip portion is interacting with the source-rock sample.

18. The method of claim 17, wherein determining via AFM the thermal conductivity of the source-rock sample comprises correlating the measured voltage difference with a value of a thermal conductivity indicated by the calibration curve.

19. The method of claim 17, wherein measuring the voltage difference comprises measuring a change in the voltage difference.

20. The method of claim 19, wherein generating the calibration curve comprises measuring the voltage difference across the heating element with the cantilever tip portion interacting with the standards samples.

21. A method of evaluating a geological formation, comprising:
mounting a source-rock sample from the geological formation to a sample holder of an atomic force microscopy (AFM) instrument;
identifying a region of interest of the source-rock sample; and
determining a thermal conductivity of the region via the AFM instrument in a scanning thermal microscopy (SThM) mode, wherein the AFM instrument comprises a cantilever tip, and wherein determining the thermal conductivity comprises checking a diameter or a width of the cantilever tip.

22. The method of claim 21, wherein identifying the region of interest is based on an analysis of the source-rock sample, the analysis being via a reflected-light optical image, scanning electron microscopy (SEM), energy dispersive spectroscopy (EDS), fluorescence, AFM-infrared red (IR), or Fourier-transform infrared spectroscopy (FTIR), or any combinations thereof.

23. The method of claim 21, comprising determining an indication of heat flow from the cantilever tip to a known material standard.

24. The method of claim 21, comprising determining an indication of heat flow from the cantilever tip to an environment of the AFM instrument at least 1 millimeter (mm) from the mounted source-rock sample.

25. The method of claim 21, wherein mounting the source-rock sample comprises mounting the source-rock sample with a specified orientation relative to a bedding of the source-rock sample.

26. The method of claim 21, wherein determining the thermal conductivity comprises transferring heat from the cantilever tip to the source-rock sample mounted in the sample holder.

27. The method of claim 21, comprising maintaining the cantilever tip at a constant temperature.

28. The method of claim 27, wherein the constant temperature comprises a room temperature.

29. The method of claim 27, comprising setting temperature and ramp parameters of a heating stage of the AFM instrument to heat the source-rock sample, the heating stage providing a heating ramp during the determining of the thermal conductivity.

30. The method of claim 29, comprising collecting SThM data and topography for the region at a resolution less than 1 millimeter through the heating ramp.

31. The method of claim 21, wherein determining the thermal conductivity comprises collecting SThM data for the region at a resolution less than 1 micrometer at a selected scan rate, and wherein the region comprises a width and length each less than 1 millimeter.

32. The method of claim 31, comprising collecting a topography of the region at the resolution at the selected scan rate.

33. The method of claim 32, wherein the selected scan rate comprises multiple different scan rates to give three dimensional (3D) effects.

34. The method of claim 31, wherein identifying the region of interest comprises identifying the region of interest based on a reflected-light optical image of the source-rock sample.

35. The method of claim 34, comprising:
identifying additional regions of interest of the source-rock sample via the reflected-light optical image; and
collecting SThM data for the additional regions at the resolution less than 1 micrometer and at the selected scan rate.

* * * * *